United States Patent
Baker et al.

(10) Patent No.: US 8,688,427 B2
(45) Date of Patent: Apr. 1, 2014

(54) ENZYME CATALYSTS FOR DIELS-ALDER REACTIONS

(75) Inventors: David Baker, Seattle, WA (US); Alexandre Zangellini, Seattle, WA (US); Justin Siegel, Seattle, WA (US); Jennifer St. Clair, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 13/130,260

(22) PCT Filed: Nov. 19, 2009

(86) PCT No.: PCT/US2009/065127
§ 371 (c)(1),
(2), (4) Date: Dec. 14, 2011

(87) PCT Pub. No.: WO2010/077470
PCT Pub. Date: Jul. 8, 2010

(65) Prior Publication Data
US 2012/0100594 A1    Apr. 26, 2012

Related U.S. Application Data

(60) Provisional application No. 61/116,264, filed on Nov. 19, 2008.

(51) Int. Cl.
*G01N 33/50* (2006.01)
*G01N 33/48* (2006.01)
*C12N 9/10* (2006.01)

(52) U.S. Cl.
USPC ............................... 703/11; 702/19; 435/193

(58) Field of Classification Search
None
See application file for complete search history.

(56) References Cited

U.S. PATENT DOCUMENTS

2002/0183937 A1* 12/2002 Mayo et al. .................... 702/19
2004/0106154 A1*  6/2004 Cornish ......................... 435/7.1
2006/0188958 A1*  8/2006 Fujihara et al. ............. 435/69.1

OTHER PUBLICATIONS

Zhang et al. Journal of Organic Chemistry (2008), 73(3), 889-899.*
Zhang et al. Database Caplus, Accession Number: 2006:246242 (Abstracts of Papers, 231st ACS National Meeting, Atlanta, GA, USA, Mar. 26-30, 2006).*
Scharff et al., "Crystal structure of diisopropylfluorophosphatase from Loligo vulgaris", Structure, vol. 9, pp. 493-502, Jun. 2001.
Ose et al., "Insight into a natural Diels-Alder reaction from the structure of macrophomate synthase", Nature, vol. 422, pp. 185-189, Mar. 13, 2003.
Zanghellini et al., "New algorithims and an in silico benchmark for computational enzyme design", Protein Science, vol. 15, pp. 2785-2794., 2006.
Uniprot entry Q7SIG4; Sep. 5, 2006, retrieved on Aug. 4, 2009, from the internet<URL:http://www.uniprot.org/uniprot/Q7SIG4>.
Copy of International Search Report issued in International Application No. PCT/US2009/065127 on Aug. 30, 2010, 5 pages.

* cited by examiner

*Primary Examiner* — Michael Borin
(74) *Attorney, Agent, or Firm* — Cooley LLP

(57) ABSTRACT

The present invention provides enzyme catalysts for Diels-Alder reactions, including intermolecular Diels-Alder reactions, as well as protein scaffolds for making such enzyme catalysts. In other aspects, the invention provides methods of making the enzyme catalysts, including by de novo computational design. The present invention thereby provides enzyme catalysts capable of catalyzing a desired Diels-Alder reaction, including with a specified or desired stereo-selectivity.

26 Claims, 21 Drawing Sheets

|  | Ideal Value | Deviation | # of Conformations |
|---|---|---|---|
| d | 2.0Å | 0.1 Å | 1 |
| $\theta_1$ | 180.0° | 10.0° | 1 |
| $\theta_2$ | 120.0° | 10.0° | 3 |
| $\chi_1$ | Free | Every 10° | 36 |
| $\chi_2$ | Free | Every 10° | 36 |
| $\chi_3$ | 180.0° | +/- 180.0° | 2 |
| $\chi'_1$ | 60°/-180°/-60° | +/- 10.0° | 21 |
| $\chi'_2$ | 60°/0°/-60° | +/- 20.0° | 21 |
| $\chi'_3$ (GLN only) | 60°/0°/-60° | +/- 20.0° | 21 |
| All |  |  | 75442752 |

|  | Ideal Value | Deviation | # of Conformations |
|---|---|---|---|
| D | 2.8 Å | 0.1 Å | 1 |
| $\theta_1$ | 120.0° | 10.0° | 1 |
| $\theta_2$ | 109.5° | 10.0° | 1 |
| $\chi_1$ | 180.0° | +/- 180.0° | 2 |
| $\chi_2$ | Free | Every 10° | 36 |
| $\chi_3$ | Free | Every 10° | 36 |
| $\chi'_1$ | 60°/-180°/-60° | +/- 10.0° | 9 |
| $\chi'_2$ | 0°/90° | +/- 20.0° | 9 |
| All |  |  | 209,952 |

FIGURE 7

```
SCAFFOLD   01  MEIPVIEPLFTKVTEDIPGA*E*GPVFDKNGDFYIVAP*E*VEVNGKPAGEILRIDLKTGKKTV   60
DA_20_00   01  MEIPVIEPLFTKVTEDIPGA*A*GPVFDKNGDFYIVAP*Y*VEVNGKPAGEILRIDLKTGKKTV   60

SCAFFOLD   61  ICKPEVNGYGGIPAGCQCDRDANQLFVADMRLGLLVVQTDGTFEEIAKKDSEGRRMQGC*N*   120
DA_20_00   61  ICKPEVNGYGGIPAGCQCDRDANQLFVADMRLGLLVVQTDGTFEEIAKKDSEGRRMQGC*A*   120

SCAFFOLD  121  *D*CAFDYEGNLWITAPAGEVAPAD*YTRSM*QEKFGSIYCFTTDGQMIQVDTAFQ*FPNG*IAVR   180
DA_20_00  121  ▓CAFDYEGNLWITAPAGEVAPAD*FTISL*QEKFGSIYCFTTDGQMIQVDTAFQ*APAG*IAVR   180

SCAFFOLD  181  HMNDGRPYQLIVAE*T*PTKKLMSYDIKGPAKIENKKVWGHIPGTH*E*GGA*D*GMDFDEDNNLL   240
DA_20_00  181  HMNDGRPYQLIVAE*T*▓PTKKLMSYDIKGPAKIENKKVWGHIPGTH*K*GGA*A*GMDFDEDNNLL   240

SCAFFOLD  241  VANWGSSHIEVFGPDGGQPKMRIRCPFFEKPS*N*LHFKPQTKTIFVTEHENNAVWKFEWQRN   300
DA_20_00  241  VANWGSSHIEVFGPDGGQPKMRIRCPFFEKPS*AL*HFKPQTKTIFVTEHENNAVWKFEWQRN   300

SCAFFOLD  301  GKKQYCETLKFGIF   314
DA_20_00  301  GKKQYCETLKFGIF   314
```

FIGURE 12

```
20_00   01  MEIPVIEPLFTKVTEDIPGAAGPVFDKNGDFYIVAPYVEVNGKPAGEILRIDLKTGKKTV   60
20_04   01  MEIPVIEPLFTKVTEDIPGATGPVFDKNGDFYIVAPYVEVNGKPAGEILRIDLKTGKKTV   60

20_00   61  ICKPEVNGYGGIPAGCQCCDRDANQLFVADMRLGLLVVQTDGTFEEIAKKDSEGRRMQGCA  120
20_04   61  ICKPEVNGYGGIPIGCQCCDRDANQLFVADMRLGLLVVQTDGTFEEIAKKDSEGRRMQGCA  120

20_00  121  YCAFDYEGNLWITAPAGEVAPADFTISLQEKFGSIYCFTTDGQMIQVDTAFQAPAGIAVR  180
20_04  121  YCAFDYEGNLWITAPAGEVAPADFTISLQEKFGSIYCFTTDGQMIQVDTAFQAPAGIAVR  180

20_00  181  HMNDGRPYQLIVAEQPTKKLWSYDIKGPAKIENKKVWGHIPGTHKGAAGMDFDEDNNLL   240
20_04  181  HMNDGRPYQLIVAEQPTKKLWSYDIKGPAKIENKKVWGHIPGTHKGAAGMDFDEDNNLL   240

20_00  241  VANWGSSHIEVFGPDGGQPKMRIRCPFEKPSALHFKPQTKTIFVTEHENNAVWKFEWQRN  300
20_04  241  VANWGSSHIEVFGPDGGQPKMRIRCPFEKPAALHFKPQTKTIFVTEHENNAVWKFEWQRN  300

20_00  301  GKKQYCETLKFGIFGSLE  318
20_04  301  GKKQYCETLKFGIFGSLE  318
```

FIGURE 14

```
20_04   01  MEIPVIEPLFTKVTEDIPGATGPVFDKNGDFYIVAPYVEVNGKPAGEILRIDLKTGKKTV   60
20_10   01  MEIPVIEPLFTKVTEDIPGATGPVFDKNGDFYIVAPYVEVNGKPAGEILRIDLKTGKKTV   60

20_04   61  ICKPEVNGYGGIPIGCQCDRDANQLFVADMRLGLIVVQTDGTFEEIAKKDSEGRRMQGCA  120
20_10   61  ICKPEVNGYGGIPIGCQCDRDANQLFVADMRLGLIVVQTDGTFEEIAKKDSEGRRMQGCA  120

20_04  121  YCAFDYEGNLWITAPAGEVAPADFTISLQEKFGSIYCFTTDGQMIQVDTAFQAPAGIAVR  180
20_10  121  YCAFDYEGNLWITAPAGEVAPADFTISLREKFGSIYCFTTDGQMIQVDTAFQCPAGIAVR  180

20_04  181  HMNDGRPYQLIVAEQPTKKLWSYDIKGPAKIENKKVWGHIPGTHKGGAAGMDFDEDNNLL  240
20_10  181  HMNDGRPYQLIVAEQPTKKLWSYDIKGPAKIENKKVWGHIPGTHKGGAAGMDFDEDNNLL  240

20_04  241  VANWGSSHIEVFGPDGGQPKMRIRCPFEKPAALHFKPQTKTIFVTEHENNAVWKFEWQRN  300
20_10  241  VANWGSSHIEVFGPDGGQPKMRIRCPFEKPAMLHFKPQTKTIFVTEHENNAVWKFEWQRN  300

20_04  301  GKKQYCETLKFGIFGSLE  318
20_10  301  GKKQYCETLKFGIFGSLE  318
```

FIGURE 17
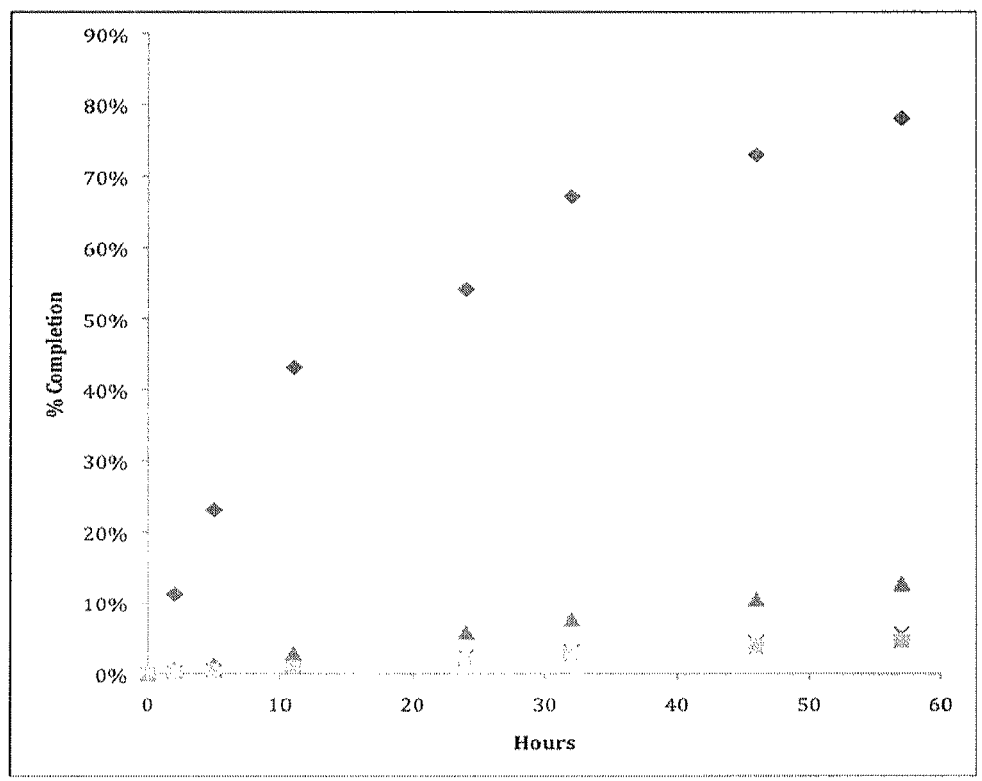
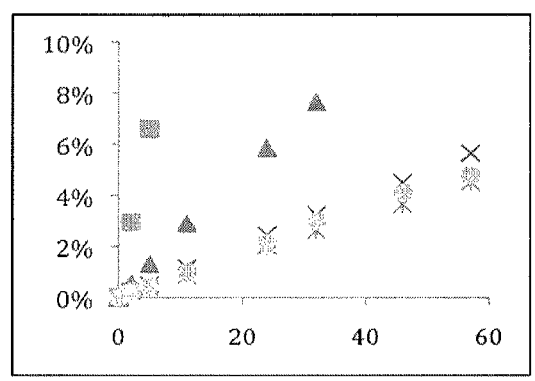

FIGURE 20

```
01  NLPTAQEVQGLMAR FIEL VDVGDIEA LVQMFADDAT VEAPFGQPP IHGRE  50
51  QIAALIRQGLKLRACLTGPVRASHNGCGAMPYRVEMVWNGQPCAIDAIAV 100
101 MRFDEHGRIQTMQQYFSKVNQSV                              123
```

FIGURE 21
1) 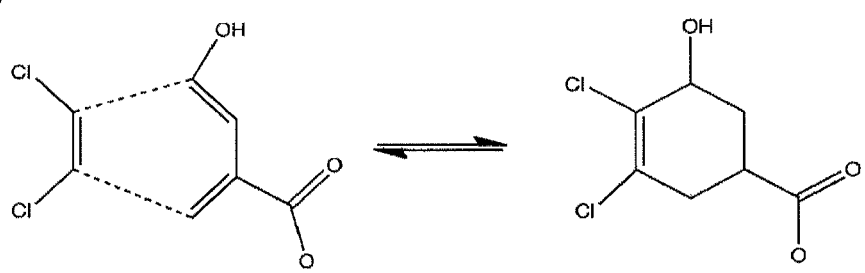
2) 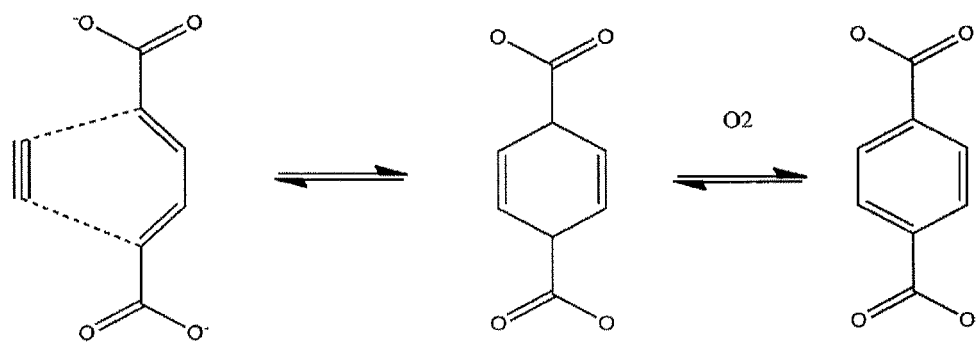
3) 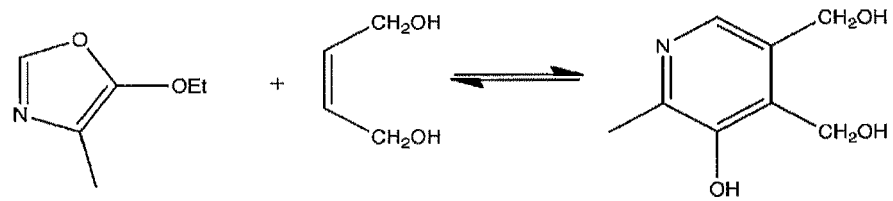
4)

SEQUENCE LISTING

<160> NUMBER OF SEQ ID NOS: 9

<210> SEQ ID NO 1
<211> LENGTH: 942
<212> TYPE: DNA
<213> ORGANISM: Loligo vulgaris

<400> SEQUENCE: 1

```
atggaaattc cagttatcga acctcttttc acaaaagtga ccgaagatat accaggtgca      60
gagggtcccg tttttgacaa aaatggcgat ttttatatcg tggcccccga agttgaagtt     120
aacggaaaac cggcgggaga aattctacga atcgatttga aaacaggaaa gaaaactgtg     180
atctgcaaac cagaagttaa tggttatgga ggaattcctg ctggctgcca atgtgatcga     240
gatgccaacc agctgtttgt ggccgacatg agactcggct tgttggtcgt gcaaactgat     300
gggacctttg aagagattgc caaaaaagac tctgaaggta gaagaatgca gggatgcaat     360
gattgcgcat tgattatga aggtaacttg tggatcactg caccagctgg ggaagtcgca     420
cctgcagact acaccgttc aatgcaggaa aaatttggca gtatttactg cttcacaaca     480
gatggtcaaa tgattcaagt ggatactgct ttccagtttc caatggtat tgctgttcgt     540
cacatgaacg atggccgtcc ttaccaacta attgtggctg aaactccaac caagaaactc     600
tggagttatg atatcaaagg tccagcaaag attgaaaaca agaaagtgtg gggtcacatc     660
ccaggtactc atgaaggtgg tgctgatgga atggattttg atgaagacaa taaccttttg     720
gtagccaact gggggagctc acacatcgaa gtgttcggcc cagatggggg acagcctaaa     780
atgagaatcc gttgcccatt tgaaaaaccc agcaacttgc atttcaagcc ccagaccaaa     840
accattttg tcacggaaca cgagaacaat gctgtctgga gtttgaatg gcaaagaaat     900
ggcaaaaaac agtattgtga gacgttaaaa tttggaatat tt                        942
```

<210> SEQ ID NO 2
<211> LENGTH: 314
<212> TYPE: PRT
<213> ORGANISM: Loligo vulgaris

<400> SEQUENCE: 2

```
Met Glu Ile Pro Val Ile Glu Pro Leu Phe Thr Lys Val Thr Glu Asp
 1               5                  10                  15
```

| | | | | | | | | | | | |
|---|---|---|---|---|---|---|---|---|---|---|---|
|Ile|Pro|Gly|Ala|Glu|Gly|Pro|Val|Phe|Asp|Lys|Asn|Gly|Asp|Phe|Tyr|
| |20| | | |25| | | |30| | |

Ile Pro Gly Ala Glu Gly Pro Val Phe Asp Lys Asn Gly Asp Phe Tyr
            20                  25                  30

Ile Val Ala Pro Glu Val Glu Val Asn Gly Lys Pro Ala Gly Glu Ile
        35                  40                  45

Leu Arg Ile Asp Leu Lys Thr Gly Lys Lys Thr Val Ile Cys Lys Pro
    50                  55                  60

Glu Val Asn Gly Tyr Gly Gly Ile Pro Ala Gly Cys Gln Cys Asp Arg
65                  70                  75                  80

Asp Ala Asn Gln Leu Phe Val Ala Asp Met Arg Leu Gly Leu Leu Val
                85                  90                  95

Val Gln Thr Asp Gly Thr Phe Glu Glu Ile Ala Lys Lys Asp Ser Glu
            100                 105                 110

Gly Arg Arg Met Gln Gly Cys Asn Asp Cys Ala Phe Asp Tyr Glu Gly
        115                 120                 125

Asn Leu Trp Ile Thr Ala Pro Ala Gly Glu Val Ala Pro Ala Asp Tyr
    130                 135                 140

Thr Arg Ser Met Gln Glu Lys Phe Gly Ser Ile Tyr Cys Phe Thr Thr
145                 150                 155                 160

Asp Gly Gln Met Ile Gln Val Asp Thr Ala Phe Gln Phe Pro Asn Gly
                165                 170                 175

Ile Ala Val Arg His Met Asn Asp Gly Arg Pro Tyr Gln Leu Ile Val
            180                 185                 190

Ala Glu Thr Pro Thr Lys Lys Leu Trp Ser Tyr Asp Ile Lys Gly Pro
        195                 200                 205

Ala Lys Ile Glu Asn Lys Lys Val Trp Gly His Ile Pro Gly Thr His
    210                 215                 220

Glu Gly Gly Ala Asp Gly Met Asp Phe Asp Glu Asp Asn Asn Leu Leu
225                 230                 235                 240

Val Ala Asn Trp Gly Ser Ser His Ile Glu Val Phe Gly Pro Asp Gly
                245                 250                 255

Gly Gln Pro Lys Met Arg Ile Arg Cys Pro Phe Glu Lys Pro Ser Asn
            260                 265                 270

Leu His Phe Lys Pro Gln Thr Lys Thr Ile Phe Val Thr Glu His Glu
        275                 280                 285

Asn Asn Ala Val Trp Lys Phe Glu Trp Gln Arg Asn Gly Lys Lys Gln
    290                 295                 300

Tyr Cys Glu Thr Leu Lys Phe Gly Ile Phe
305                 310

<210> SEQ ID NO 3
<211> LENGTH: 972
<212> TYPE: DNA
<213> ORGANISM: Artificial Sequence
<220> FEATURE:
<223> OTHER INFORMATION: Enzyme catalyst for Diels-Alder reaction

<400> SEQUENCE: 3

```
atggaaatcc cggtgatcga gccgctgttc actaaagtga ccgaagacat cccgggtgct      60
gcgggtccgg ttttcgataa aaacggcgat ttttatattg tggcgccgta cgtagaagtt     120
aacgggaaac cggccggtga aattctgcgc atcgatctga aaaccggtaa gaaaacggtt     180
atctgcaaac cggaagtaaa cggctatggt ggcatcccgg cggatgtcaa atgcgaccgt     240
gatgcgaatc agctgtttgt ggcggatatg cgcctgggtc tgctggtcgt acagacggat     300
gggacgtttg aagagattgc taaaaaagat cggaaggtc gccgtatgca gggctgtgca     360
tattgtgcat tcgattatga agggaacctg tggatcaccg ctccggcggg tgaagttgcc     420
```

-continued

```
ccggcggatt ttacgatttc actgcaggag aaatttggct ctatctattg ttttactacc    480
gatggtcaga tgattcaggt ggataccgcg ttccaagcac cggcgggtat tgccgtccgc    540
cacatgaacg atggtcgtcc gtatcaactg attgttgcgg aacaaccgac aaaaaagctg    600
tggtcttacg atattaaagg cccagcaaaa attgagaaca aaaagtttg gggccacatt     660 cctggtacgc acaaaggtgg cgccgcgggt atggattttg atgaggataa caacctgctg    720
gtcgcgaatt ggggtagctc ccatattgaa gtctttggtc ctgatggagg ccagccgaaa    780
atgcgtatcc gttgccccttt tgaaaaaccg agtgcactgc atttcaagcc gcagacgaaa    840
actattttcg ttacggaaca cgaaaacaat gcggtttgga atttgaatg cagcgtaat     900 ggtaaaaagc aatattgcga aaccctgaaa tttggcattt ttggttccct cgagcatcat    960
catcatcatc at                                                         972
```

<210> SEQ ID NO 4
<211> LENGTH: 324
<212> TYPE: PRT
<213> ORGANISM: Artificial Sequence
<220> FEATURE:
<223> OTHER INFORMATION: Enzyme catalyst for Diels-Alder reaction

<400> SEQUENCE: 4

```
Met Glu Ile Pro Val Ile Glu Pro Leu Phe Thr Lys Val Thr Glu Asp
1               5                   10                  15

Ile Pro Gly Ala Ala Gly Pro Val Phe Asp Lys Asn Gly Asp Phe Tyr
            20                  25                  30

Ile Val Ala Pro Tyr Val Glu Val Asn Gly Lys Pro Ala Gly Glu Ile
        35                  40                  45

Leu Arg Ile Asp Leu Lys Thr Gly Lys Lys Thr Val Ile Cys Lys Pro
    50                  55                  60

Glu Val Asn Gly Tyr Gly Gly Ile Pro Ala Gly Cys Gln Cys Asp Arg
65                  70                  75                  80

Asp Ala Asn Gln Leu Phe Val Ala Asp Met Arg Leu Gly Leu Leu Val
                85                  90                  95

Val Gln Thr Asp Gly Thr Phe Glu Glu Ile Ala Lys Lys Asp Ser Glu
            100                 105                 110

Gly Arg Arg Met Gln Gly Cys Ala Tyr Cys Ala Phe Asp Tyr Glu Gly
        115                 120                 125

Asn Leu Trp Ile Thr Ala Pro Ala Gly Glu Val Ala Pro Ala Asp Phe
    130                 135                 140

Thr Ile Ser Leu Gln Glu Lys Phe Gly Ser Ile Tyr Cys Phe Thr Thr
145                 150                 155                 160

Asp Gly Gln Met Ile Gln Val Asp Thr Ala Phe Gln Ala Pro Ala Gly
                165                 170                 175

Ile Ala Val Arg His Met Asn Asp Gly Arg Pro Tyr Gln Leu Ile Val
            180                 185                 190

Ala Glu Gln Pro Thr Lys Lys Leu Trp Ser Tyr Asp Ile Lys Gly Pro
        195                 200                 205

Ala Lys Ile Glu Asn Lys Lys Val Trp Gly His Ile Pro Gly Thr His
    210                 215                 220

Lys Gly Gly Ala Ala Gly Met Asp Phe Asp Glu Asp Asn Asn Leu Leu
225                 230                 235                 240

Val Ala Asn Trp Gly Ser Ser His Ile Glu Val Phe Gly Pro Asp Gly
                245                 250                 255

Gly Gln Pro Lys Met Arg Ile Arg Cys Pro Phe Glu Lys Pro Ser Ala
```

```
                260               265               270
Leu His Phe Lys Pro Gln Thr Lys Thr Ile Phe Val Thr Glu His Glu
            275                 280                 285

Asn Asn Ala Val Trp Lys Phe Glu Trp Gln Arg Asn Gly Lys Lys Gln
        290                 295                 300

Tyr Cys Glu Thr Leu Lys Phe Gly Ile Phe Gly Ser Leu Glu His His
305                 310                 315                 320

His His His His

<210> SEQ ID NO 5
<211> LENGTH: 972
<212> TYPE: DNA
<213> ORGANISM: Artificial Sequence
<220> FEATURE:
<223> OTHER INFORMATION: Enzyme catalyst for Diels-Alder reaction

<400> SEQUENCE: 5
atggaaatcc cggtgatcga gccgctgttc actaaagtga ccgaagacat cccgggtgct    60
acgggtccgg ttttcgataa aaacggcgat ttttatattg tggcgccgta cgtagaagtt   120
aacgggaaac cggccggtga aattctgcgc atcgatctga aaccggtaa  gaaaacggtt   180 atctgcaaac cggaagtaaa cggctatggt ggcatcccga taggatgtca atgcgaccgt   240
gatgcgaatc agctgtttgt ggcggatatg cgcctgggtc tgctggtcgt acagacggat   300
gggacgtttg aagagattgc taaaaaagat tcggaaggtc gccgtatgca gggctgtgca   360
tattgtgcat tcgattatga agggaacctg tggatcaccg ctccggcggg tgaagttgcc   420
ccggcggatt ttacgatttc actgcaggag aaatttggct ctatctattg ttttactacc   480
gatggtcaga tgattcaggt ggataccgcg ttccaagcac cggcgggtat tgccgtccgc   540
cacatgaacg atggtcgtcc gtatcaactg attgttgcgg acaaccgac  aaaaaagctg   600 tggtcttacg atattaaagg cccagcaaaa attgagaaca aaaagtttg  gggccacatt   660 cctggtacgc acaaaggtgg cgccgcgggt atggattttg atgaggataa caacctgctg   720
gtcgcgaatt ggggtagctc ccatattgaa gtctttggtc ctgatggagg ccagccgaaa   780
atgcgtatcc gttgcccttt tgaaaaaccg gctgcactgc atttcaagcc gcagacgaaa   840
actattttcg ttacggaaca cgaaaacaat gcggtttgga aatttgaatg cagcgtaat    900 ggtaaaaagc aatattgcga aaccctgaaa tttggcattt ttggttccct cgagcatcat   960
catcatcatc at                                                       972

<210> SEQ ID NO 6
<211> LENGTH: 324
<212> TYPE: PRT
<213> ORGANISM: Artificial Sequence
<220> FEATURE:
<223> OTHER INFORMATION: Enzyme catalyst for Diels-Alder reaction

<400> SEQUENCE: 6

Met Glu Ile Pro Val Ile Glu Pro Leu Phe Thr Lys Val Thr Glu Asp
1               5                   10                  15

Ile Pro Gly Ala Thr Gly Pro Val Phe Asp Lys Asn Gly Asp Phe Tyr
            20                  25                  30

Ile Val Ala Pro Tyr Val Glu Val Asn Gly Lys Pro Ala Gly Glu Ile
        35                  40                  45

Leu Arg Ile Asp Leu Lys Thr Gly Lys Lys Thr Val Ile Cys Lys Pro
    50                  55                  60

Glu Val Asn Gly Tyr Gly Gly Ile Pro Ile Gly Cys Gln Cys Asp Arg
```

```
                     65                  70                  75                  80
Asp Ala Asn Gln Leu Phe Val Ala Asp Met Arg Leu Gly Leu Leu Val
                 85                  90                  95

Val Gln Thr Asp Gly Thr Phe Glu Glu Ile Ala Lys Lys Asp Ser Glu
            100                 105                 110

Gly Arg Arg Met Gln Gly Cys Ala Tyr Cys Ala Phe Asp Tyr Glu Gly
        115                 120                 125

Asn Leu Trp Ile Thr Ala Pro Ala Gly Glu Val Ala Pro Ala Asp Phe
    130                 135                 140

Thr Ile Ser Leu Gln Glu Lys Phe Gly Ser Ile Tyr Cys Phe Thr Thr
145                 150                 155                 160

Asp Gly Gln Met Ile Gln Val Asp Thr Ala Phe Gln Ala Pro Ala Gly
                165                 170                 175

Ile Ala Val Arg His Met Asn Asp Gly Arg Pro Tyr Gln Leu Ile Val
            180                 185                 190

Ala Glu Gln Pro Thr Lys Lys Leu Trp Ser Tyr Asp Ile Lys Gly Pro
        195                 200                 205

Ala Lys Ile Glu Asn Lys Lys Val Trp Gly His Ile Pro Gly Thr His
    210                 215                 220

Lys Gly Gly Ala Ala Gly Met Asp Phe Asp Glu Asp Asn Asn Leu Leu
225                 230                 235                 240

Val Ala Asn Trp Gly Ser Ser His Ile Glu Val Phe Gly Pro Asp Gly
                245                 250                 255

Gly Gln Pro Lys Met Arg Ile Arg Cys Pro Phe Glu Lys Pro Ala Ala
            260                 265                 270

Leu His Phe Lys Pro Gln Thr Lys Thr Ile Phe Val Thr Glu His Glu
        275                 280                 285

Asn Asn Ala Val Trp Lys Phe Glu Trp Gln Arg Asn Gly Lys Lys Gln
    290                 295                 300

Tyr Cys Glu Thr Leu Lys Phe Gly Ile Phe Gly Ser Leu Glu His His
305                 310                 315                 320

His His His His

<210> SEQ ID NO 7
<211> LENGTH: 972
<212> TYPE: DNA
<213> ORGANISM: Artificial Sequence
<220> FEATURE:
<223> OTHER INFORMATION: Enzyme catalyst for Diels-Alder reaction

<400> SEQUENCE: 7
atggaaatcc cggtgatcga gccgctgttc actaaagtga ccgaagacat cccgggtgct      60
acgggtccgg ttttcgataa aaacggcgat ttttatattg tggcgccgta cgtagaagtt     120
aacgggaaac cggccggtga aattctgcgc atcgatctga aaaccggtaa gaaaacggtt     180
atctgcaaac cggaagtaaa cggctatggt ggcatcccga taggatgtca atgcgaccgt     240
gatgcgaatc agctgtttgt ggcggatatg cgcctgggtc tgctggtcgt acagacggat     300
gggacgtttg aagagattgc taaaaaagat tcggaaggtc gccgtatgca gggctgtgca     360
tattgtgcat tcgattatga agggaacctg tggatcaccg ctccggcggg tgaagttgcc     420
ccggcggatt ttacgatttc actgcgggag aaatttggct ctatctattg ttttactacc     480
gatggtcaga tgattcaggt ggataccgcg ttccaatgcc ggcgggtat tgccgtccgc     540 cacatgaacg atggtcgtcc gtatcaactg attgttgcgg aacaaccgac aaaaaagctg     600
tggtcttacg atattaaagg cccagcaaaa attgagaaca aaaaagtttg ggccacatt     660
```

```
cctggtacgc acaaaggtgg cgccgcgggt atggattttg atgaggataa caacctgctg      720
gtcgcgaatt ggggtagctc ccatattgaa gtctttggtc ctgatggagg ccagccgaaa      780
atgcgtatcc gttgccctt tgaaaaaccg gctaatctgc atttcaagcc gcagacgaaa       840
actattttcg ttacggaaca cgaaaacaat gcggtttgga aatttgaatg cagcgtaat       900 ggtaaaaagc aatattgcga aaccctgaaa tttggcattt ttggttccct cgagcatcat      960
catcatcatc at                                                          972
```

```
<210> SEQ ID NO 8
<211> LENGTH: 324
<212> TYPE: PRT
<213> ORGANISM: Artificial Sequence
<220> FEATURE:
<223> OTHER INFORMATION: Enzyme catalyst for Diels-Alder reaction

<400> SEQUENCE: 8

Met Glu Ile Pro Val Ile Glu Pro Leu Phe Thr Lys Val Thr Glu Asp
1               5                   10                  15

Ile Pro Gly Ala Thr Gly Pro Val Phe Asp Lys Asn Gly Asp Phe Tyr
            20                  25                  30

Ile Val Ala Pro Tyr Val Glu Val Asn Gly Lys Pro Ala Gly Glu Ile
        35                  40                  45

Leu Arg Ile Asp Leu Lys Thr Gly Lys Lys Thr Val Ile Cys Lys Pro
    50                  55                  60

Glu Val Asn Gly Tyr Gly Gly Ile Pro Ile Gly Cys Gln Cys Asp Arg
65                  70                  75                  80

Asp Ala Asn Gln Leu Phe Val Ala Asp Met Arg Leu Gly Leu Leu Val
                85                  90                  95

Val Gln Thr Asp Gly Thr Phe Glu Glu Ile Ala Lys Lys Asp Ser Glu
            100                 105                 110

Gly Arg Arg Met Gln Gly Cys Ala Tyr Cys Ala Phe Tyr Glu Gly
        115                 120                 125

Asn Leu Trp Ile Thr Ala Pro Ala Gly Glu Val Ala Pro Ala Asp Phe
    130                 135                 140

Thr Ile Ser Leu Arg Glu Lys Phe Gly Ser Ile Tyr Cys Phe Thr Thr
145                 150                 155                 160

Asp Gly Gln Met Ile Gln Val Asp Thr Ala Phe Gln Cys Pro Ala Gly
                165                 170                 175

Ile Ala Val Arg His Met Asn Asp Gly Arg Pro Tyr Gln Leu Ile Val
            180                 185                 190

Ala Glu Gln Pro Thr Lys Lys Leu Trp Ser Tyr Asp Ile Lys Gly Pro
        195                 200                 205

Ala Lys Ile Glu Asn Lys Lys Val Trp Gly His Ile Pro Gly Thr His
    210                 215                 220

Lys Gly Gly Ala Ala Gly Met Asp Phe Asp Glu Asp Asn Asn Leu Leu
225                 230                 235                 240

Val Ala Asn Trp Gly Ser Ser His Ile Glu Val Phe Gly Pro Asp Gly
                245                 250                 255

Gly Gln Pro Lys Met Arg Ile Arg Cys Pro Phe Glu Lys Pro Ala Asn
            260                 265                 270

Leu His Phe Lys Pro Gln Thr Lys Thr Ile Phe Val Thr Glu His Glu
        275                 280                 285

Asn Asn Ala Val Trp Lys Phe Glu Trp Gln Arg Asn Gly Lys Lys Gln
    290                 295                 300
```

-continued

```
Tyr Cys Glu Thr Leu Lys Phe Gly Ile Phe Gly Ser Leu Glu His His
305                 310                 315                 320

His His His His

<210> SEQ ID NO 9
<211> LENGTH: 123
<212> TYPE: PRT
<213> ORGANISM: Artificial Sequence
<220> FEATURE:
<223> OTHER INFORMATION: Enzyme catalyst for Diels-Alder reaction

<400> SEQUENCE: 9

Asn Leu Pro Thr Ala Gln Glu Val Gln Gly Leu Met Ala Arg Phe Ile
1               5                   10                  15

Glu Leu Val Asp Val Gly Asp Ile Glu Ala Leu Val Gln Met Phe Ala
                20                  25                  30

Asp Asp Ala Thr Val Glu Ala Pro Phe Gly Gln Pro Pro Ile His Gly
            35                  40                  45

Arg Glu Gln Ile Ala Ala Leu Ile Arg Gln Gly Leu Lys Leu Arg Ala
        50                  55                  60

Cys Leu Thr Gly Pro Val Arg Ala Ser His Asn Gly Cys Gly Ala Met
65                  70                  75                  80

Pro Tyr Arg Val Glu Met Val Trp Asn Gly Gln Pro Cys Ala Ile Asp
                85                  90                  95

Ala Ile Ala Val Met Arg Phe Asp Glu His Gly Arg Ile Gln Thr Met
                100                 105                 110

Gln Gln Tyr Phe Ser Lys Val Asn Gln Ser Val
            115                 120
```

ENZYME CATALYSTS FOR DIELS-ALDER REACTIONS

PRIORITY

This application is a U.S. National Phase of International Application No. PCT/US2009/065127, filed Nov. 19, 2009, which claims priority to U.S. Provisional Application No. 61/116,264, filed Nov. 19, 2008, the disclosure of which are hereby incorporated by reference in their entireties.

GOVERNMENT RIGHTS

This invention was made with government support under HR0011-08-1-0085 awarded by the Defense Advanced Research Projects Agency (DARPA), and F49620-03-1-0110 (P03) awarded by the Air Force Office of Scientific Research (AFOSR/JA). The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ARZE_002_01US_SeqList_ST25.txt, date recorded: May 19, 2011, file size 19 kilobytes).

BACKGROUND

The Diels-Alder reaction is a cycloaddition reaction between a conjugated diene and a substituted alkene or alkyne (e.g., a dienophile), to form a substituted cyclohexene system. The reaction forms two carbon-carbon bonds and up to four new stereogenic centers in one step. Since its discovery, the Diels-Alder reaction has been a cornerstone reaction for the synthesis of organic compounds.

The mechanisms of substituent effects on Diels-Alder reactivity are well understood (30) and the potential for accelerating the reaction by raising the HOMO (highest occupied molecular orbital) energy of the diene, lowering the LUMO (lowest unoccupied molecular orbital) energy of the dienophile, in addition to approximation, provides an attractive target for catalysis. Indeed, several protein catalysts for this reaction have been reported, elicited by immune response against two different transition state analogs (31,32). Experimental studies and quantum mechanical calculations on model systems for the reactions catalyzed indicate that these function by increasing hydrogen-bond strength in the transition state and binding two reactants in an arrangement suitable for reaction (10).

Despite the fact that the Diels-Alder reaction is one of the main chemical routes to make carbon-carbon bonds (e.g., in addition to step-wise aldol condensation), there has been little firm evidence of its use by living organisms as opposed to the many aldolases that have been characterized (33). So far, three natural enzymes have been proposed to catalyze a Diels-Alder reaction, although for some of them the exact mechanism is still debated (34,35,36,37,38,39,40). Consequently, there is no definite evidence of the existence of a natural, bimolecular Diels-Alderase enzyme.

Two different families of synthetic ribozymes (RNA catalysts) have been engineered to date. A library of RNA molecules was created covalently attached to an acyclic diene and selected for Diels-Alder activity (41,42). The best ribozymes showed rate enhancements of up to 800-fold over the uncatalyzed reaction. Since one of the substrates is covalently attached to the RNA catalyst, the reaction is effectively first order and the author reported a $k_{cat}/K_M$ of 3.95 $M^{-1}s^{-1}$ and an effective molarity of 2M. Similar results were obtained using a library of PEG-ylated RNA molecules attached to anthracene and directed to catalyze a Diels-Alder reaction with a maleimide dienophile (43).

A handful of catalytic antibodies have also been elicited for Diels-Alder reactions between various compounds. For example, antibody 1E9 catalyzes the addition of tetrachlorothiophene dioxide and N-ethyl maleimide (44,45). 1E9 is the most effective Diels-Alder catalyzing antibody known to date, with a catalytic proficiency of $10^7$ $M^{-1}$ and an effective molarity of $10^3$ M (27). In addition, multiple turnovers were observed with antibody 1E9, and a crystal structure was solved showing the molecular details of the active site. Similarly, antibody 39-A11 catalyzes the Diels-Alder reaction between an electron-rich acyclic diene and an N-aryl maleimide (46), although its proficiency is lower due to a less complimentary binding pocket. Finally, antibodies 4D5, 13G5, and several others, were shown to catalyze regio-, diastereo- and enantio-selective addition of 4-carboxybenzyl trans-1,3-butadiene-1-carbamate and N,N-dimethylacrylamide, a model Diels-Alder reaction (10).

The ability to design selective catalysts, including stereoselective catalysts, for the Diels-Alder reaction would be extremely valuable for chemical synthesis. While, an approach for computation enzyme design has been described (Zanghellini et al., *New Algorithms and an in silico Benchmark for Computational Enzyme Design, Protein Science* 15:2785-2794 (2006)), computational de novo design of an enzyme catalyzing a bimolecular reaction such as a Diels Alder reaction has not been described.

SUMMARY OF THE INVENTION

The present invention provides enzyme catalysts for Diels-Alder reactions, including intermolecular Diels-Alder reactions, as well as protein scaffolds for making such enzyme catalysts. In other aspects, the invention provides methods of making the enzyme catalysts, including by de novo computational design. The present invention thereby provides enzyme catalysts capable of catalyzing a desired Diels-Alder reaction, including with a specified or desired stereo-selectivity.

In one aspect, the present invention provides enzyme catalysts for Diels-Alder reactions. The enzymes have scaffolds derived from non-immunoglobulin amino acid sequences, such as diisopropylfluorophosphatase from *Loligo vulgaris* (PDB-ID 1E1A) (or a homolog thereof), or ketosteroid isomerase *Pseudomonas putida* (PDB-ID 1OHO) (or a homolog thereof). Alternative exemplary scaffolds are disclosed herein in Table 1. The Diels-Alder scaffold has a pocket designed and/or adapted to catalyze a Diels-Alder reaction, as disclosed in detail herein. Active site residues in each case, and with respect to the desired substrates, may be identified using computational tools known in the art and described herein. In some embodiments, the enzyme active site comprises amino acid side chains positioned to act as electron-withdrawing and/or electron-donating groups to stabilize the Diels-Alder transition state, and/or contains a substrate-binding pocket having hydrophobic and/or polar interfaces that accommodate the Diels-Alder reaction by binding the substrates in the proper orientation for catalysis.

In certain embodiments, the active site comprises one or more amino acid side chains positioned to stabilize the Diels-Alder transition state by hydrogen-bond acceptor and/or donor groups. For example, the active site may contain an amino acid residue having a side chain that stabilizes the Diels-Alder transition state by accepting a hydrogen-bond from the diene portion of the transition state, or from the dienophile portion of the transition state. As exemplified herein for a Diels-Alder reaction and the scaffold of SEQ ID NO:2, such an amino acid residue may be at the position corresponding to position 195 of the diisopropylfluorophosphatase scaffold (SEQ ID NO:2). An amino acid residue having a side chain that stabilizes the Diels-Alder transition state by donating a hydrogen-bond to the dienophile portion of the transition state, or to the diene portion of the transition state, may be at the position corresponding to position 121 of the scaffold of SEQ ID NO:2. Alternatively or in addition, the active site accommodates the Diels-Alder substrates in the proper orientation for catalysis.

In other embodiments utilizing a ketosteroid isomerase scaffold, the active site may contain an amino acid residue having a side chain that accepts a hydrogen bond from the Diels-Alder transition state, and such amino acid may be at the position corresponding to position 82 of the scaffold (e.g., SEQ ID NO:9). The active site may also contain an amino acid residue that donates a hydrogen-bond to the Diels-Alder transition state, and such amino acid residue may be at the position corresponding to position 114 of the scaffold (e.g., SEQ ID NO:9). Alternatively or in addition, the active site accommodates the Diels-Alder substrates in the proper orientation for catalysis.

The Diels-Alder enzyme catalyst; in addition to having the catalytic amino acid(s) on the protein scaffold in the proper position(s) to stabilize the Diels-Alder transition state, also contains an active site pocket with a tight complementary surface to sufficiently accommodate, not only the desired substrate(s), but also the transition state and resulting product. For example, the active site may provide additional contacts to the substrate(s), and/or provide a complementary interface with the proper positioning of polar and non-polar amino acid side chains. In some embodiments, the active site pocket is a relatively non-polar environment (e.g., hydrophobic), lined predominately with non-polar amino acids. With respect to the scaffold of SEQ ID NO:2, amino acid residues that may influence the position of the catalytic side chains and/or influence the environment and/or shape of the active site include amino acid residues corresponding to positions 21, 36, 37, 39, 72, 74, 90, 120, 135, 136, 144, 146, 148, 149, 173, 175, 176, 196, 225, 229, 230, 244, 269, 271, 272 and 287 of the scaffold (SEQ ID NO:2). With respect to the scaffold of SEQ ID NO:9, amino acid residues that may influence the position of the catalytic side chains and/or influence the environment and/or shape of the active site include amino acid residues corresponding to positions 86, 93, 95, 121, 118, 116, 40, 43, 39, 84, 62, 59, 58, 37, 46, 55, 97, 114, 112, 99, 82, 19, 60, 64, 16, 31, 15, 80, 27, 56.

In other aspects, the invention provides methods for making enzymes that catalyze Diels-Alder reactions. The methods may involve de novo enzyme design by transition state, substrate and/or product model placement within a scaffold or scaffold library, or in other embodiments, the methods involve designing the scaffolds and Diels-Alder enzymes described herein (or homologs thereof) for desired substrates.

For de novo enzyme design, the method comprises first creating a Diels-Alder transition state, substrate, and/or product model with protein functional groups positioned to support catalysis. A protein scaffold is then identified (e.g., using hashing algorithms) that has backbone coordinates sufficient to support the positioning of the protein functional groups. Mutations are then introduced into the scaffold by rational design and/or as guided by functional Diels-Alder assays to create and improve the designs.

In other aspects, the invention involves making Diels-Alder enzymes by mutation of the scaffolds and enzymes described herein (or homologs thereof) to accommodate desired Diels-Alder substrates.

BRIEF DESCRIPTION OF THE DRAWINGS

FIG. 7 shows the sequence of the scaffold aligned with the original design for the Diels-Alder catalyzing enzyme (DA_20_00, SEQ ID NO:4)). The scaffold is diisopropylfluorophosphatase from *Loligo vulgaris* (PDB-ID 1E1A). The amino acid sequence for the native scaffold is provided herein as SEQ ID NO:2. The catalytic residues in the original design are shaded, and amino acids mutated during the initial design stages are shown in bold.

Triangles indicate the location of a beta-bridge. A three-amino acid helix is located near the C-terminus.

Figure 10:
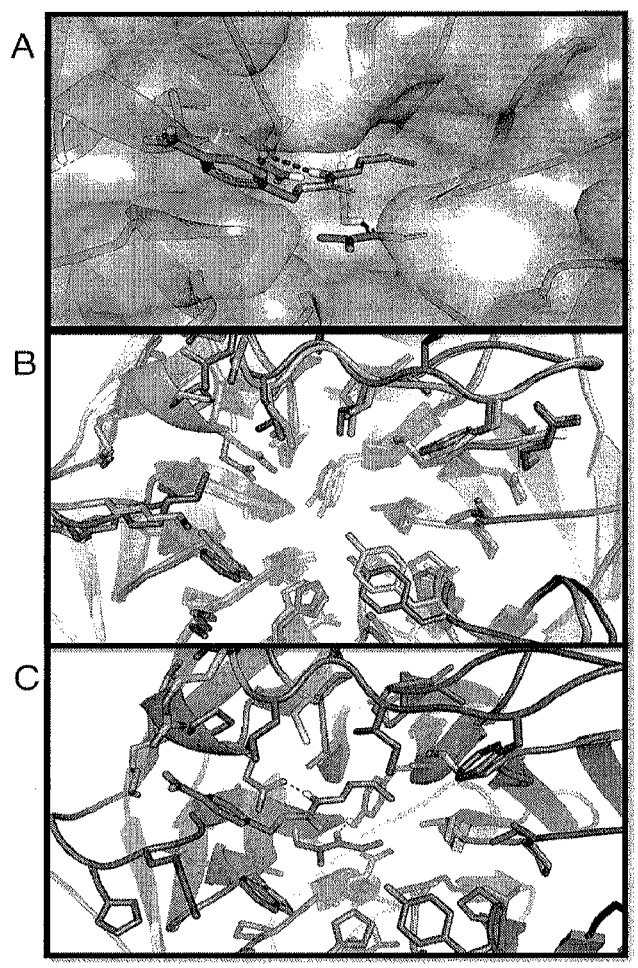

FIG. 10 illustrates the structure of the computationally designed Diels-Alderase. Top panel (A): surface view of the design model (DA_20_00) bound to the substrates (diene and dienophile). The catalytic residues making the designed hydrogen bonds are depicted as sticks. Middle panel (B): overlay of the design model (DA_20_00) and the apo enzyme crystal structure of DA_20_00_A74I. Bottom panel (C): active site view of the molecular interactions between the substrate complex and the crystal structure, repacked and minimized using ROSETTA with the additional mutations found to increase overall catalytic efficiency.

Figure 11:
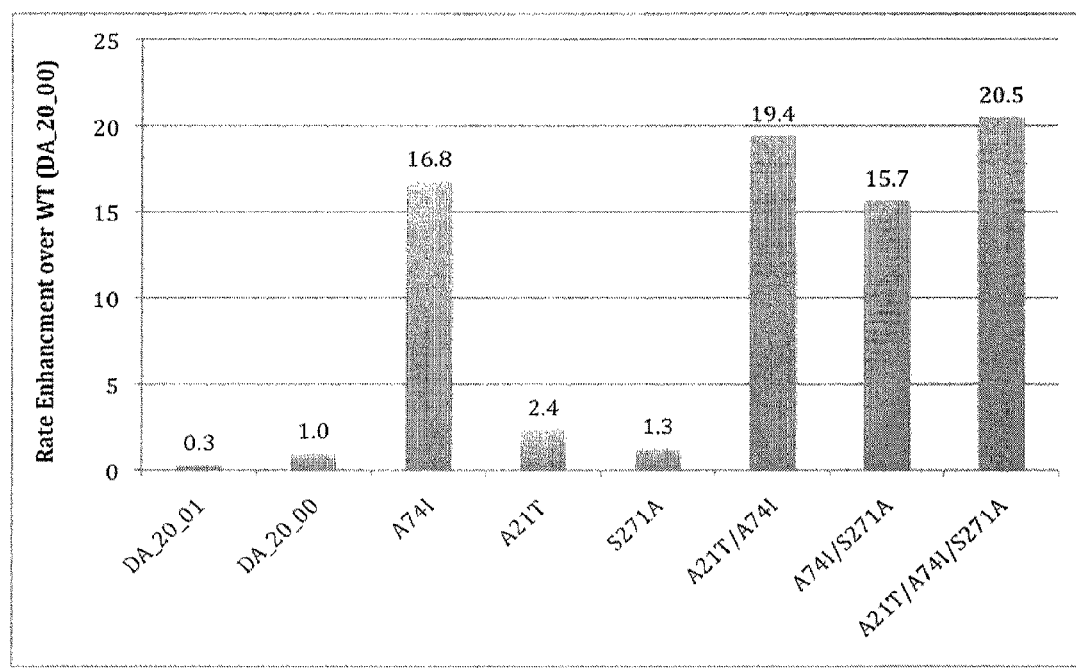

FIG. 11 shows the combinatorial mutants from round 1 active site optimization. The observed velocity for each mutant was normalized by the velocity of DA_20_00 in order to determine the effective rate enhancement conferred by each mutation. The reactions were done at 1 mM diene, and 10 mM dienophile, PBS, 298K, and 100 µM protein.

FIG. 12 shows an alignment between DA_20_00, the initial design, and DA_20_04, the enzyme after one round of optimization. The catalytic residues Y121 and Q195 are shown shaded. Three mutations were made relative to the initial enzyme: A21I and A74I which are thought to improve packing around the transition state, and S271A, which is thought to make the dienophile environment more non-polar. The three mutations are shown in bold type.

Figure 13:
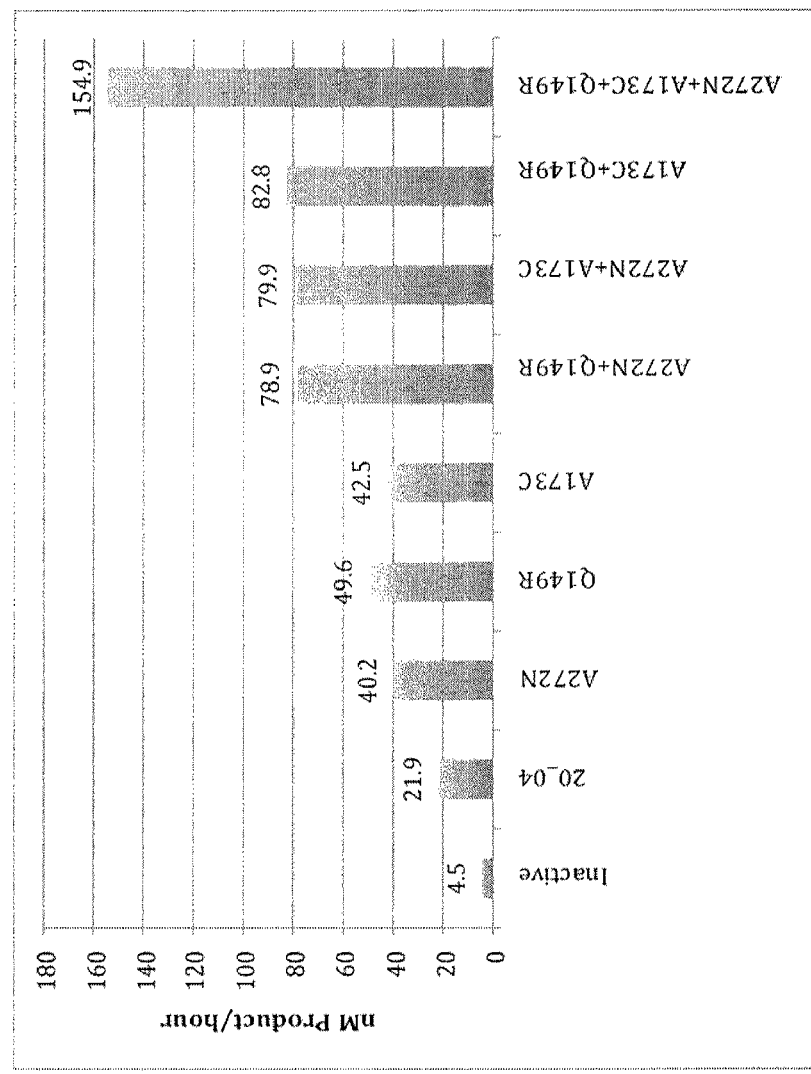

FIG. 13 shows the relative activity of selected second round mutants. Mutations showing enhanced activity on DA_20_04 were sequenced, grown large scale, and assayed. The assay was done at 0.1 mM dieine, 3 mM dienophile, PBS, 298K, and 20 µM protein.

FIG. 14 shows an alignment between DA_20_04 and DA_20_10, the enzyme after the second round of optimization. The catalytic residues Y121 and Q195 are shown shaded. Three mutations were made relative to the DA_20_04 enzyme: A173C, which is thought to improve packing around the catalytic glutamine; Q149R, which is thought to hydrogen bond to the carboxylate on the diene; and A272N, which is thought to hold the catalytic tyrosine in proper conformation for catalysis. The three mutations are shown in bold type.

Figure 15:
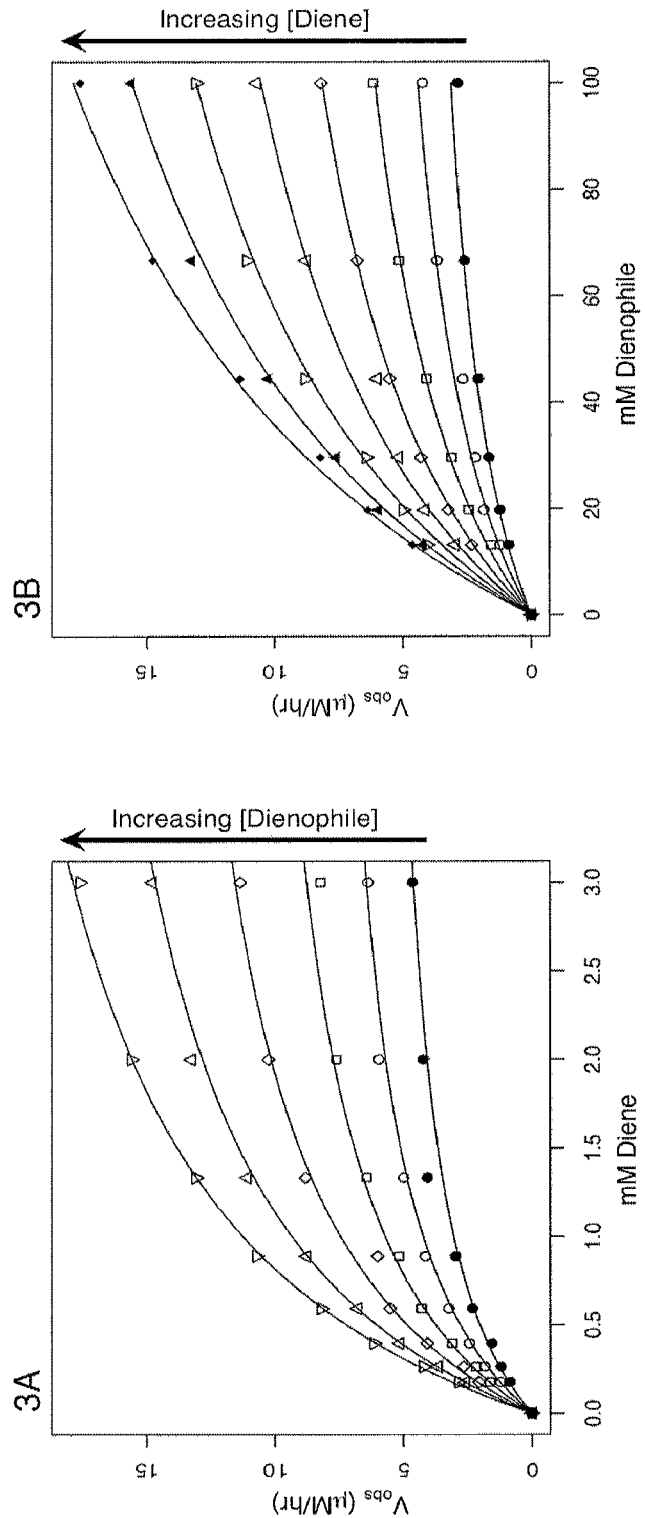

FIG. 15 shows kinetic characterization of DA_20_10. (A) Dependence of reaction velocity on diene concentration for different fixed dienophile concentrations. The diene concentration was varied from 3.0 to 0.18 mM with a fixed concentration of 100 mM (◇), 66 mM (Δ), 44 mM (◇), 30 mM (○), 20 mM (○), or 13 mM (●) dienophile (B) Dependence of reaction velocity on dienophile concentration for different fixed diene concentrations. The dienophile was varied from 100 to 13.0 mM with a fixed concentration of 3 mM (♦), 2 mM (▲), 1.3 mM (▽), 0.9 mM (Δ), 0.6 mM (◇), 0.4 mM (□), 0.26 mM (○), or 0.18 mM (●) dienophile. Reactions were carried out with 20 µM protein in PBS at 298 K.

Figure 16:
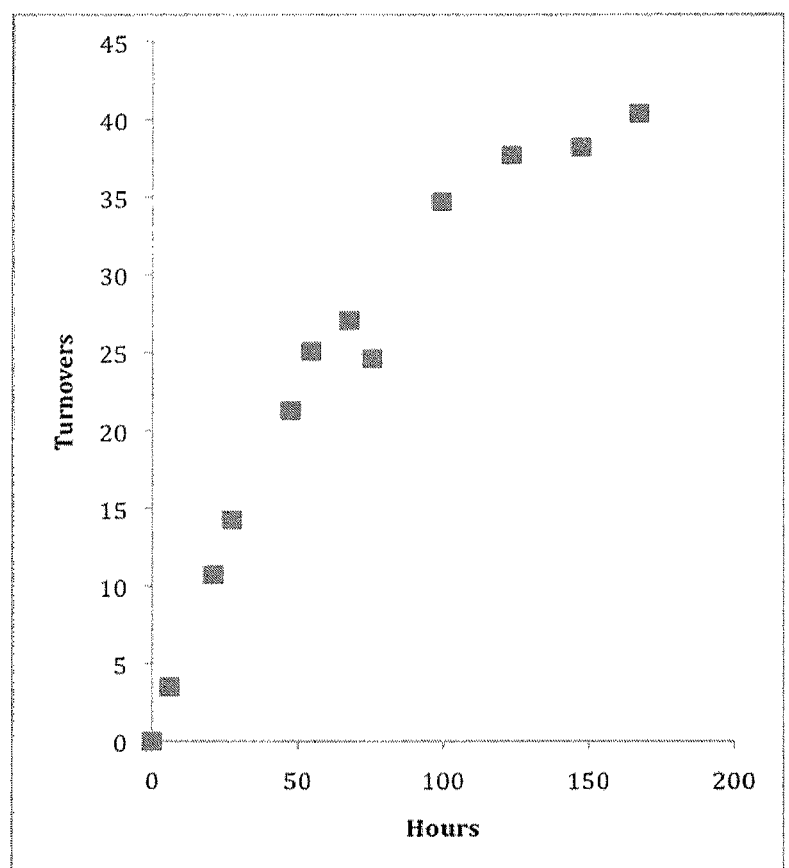

FIG. 16 shows DA_20_10 Turnover Number. The reaction was carried out in 3 mM diene, 100 mM dienophile, 25 µM enzyme, in PBS at 298K. Turnover number was calculated by subtracting the product formed in the background reaction from the product formed in the enzymatic reaction. This enzyme-produced product was then divided by the protein concentration to determine turnover number.

FIG. 17 shows production with DA_20_10 and effects of catalytic residues. The reaction was carried out in 1 mM diene, 50 mM dienophile, 200 µM enzyme, in PBS at 298K. The proteins assayed are DA_20_10 (υ), Y121F (▲), Q195E (x), and tela scaffold (*), uncatalyzed (λ).

Figure 18:
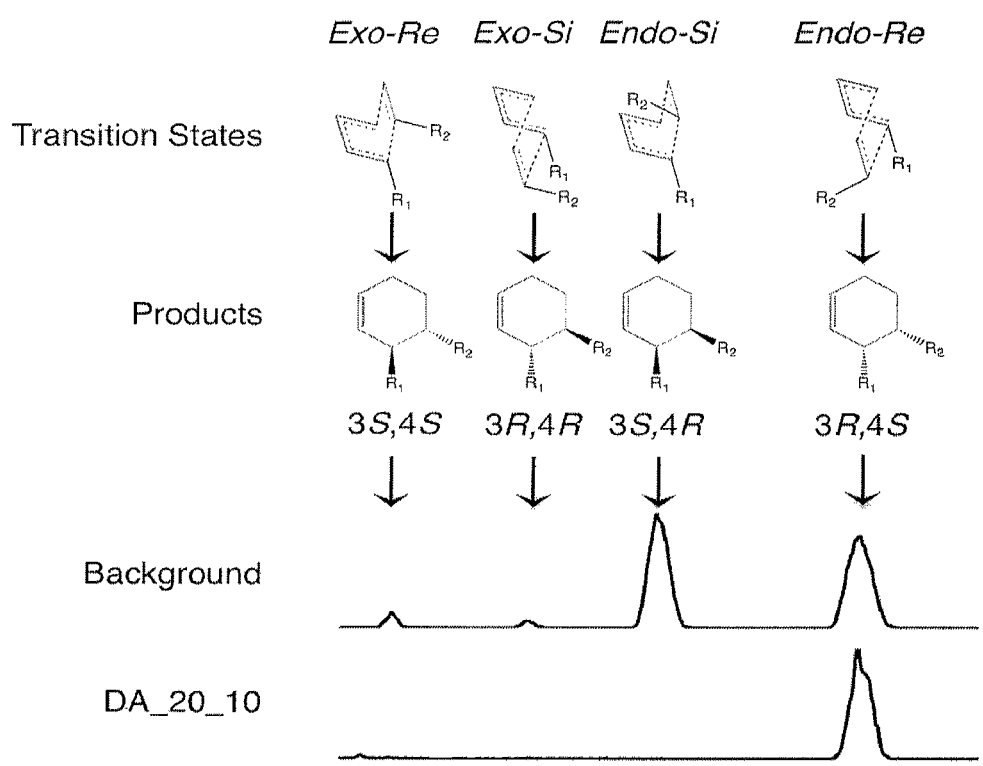

FIG. 18 shows the absolute stereoselectivity of DA_20_10. The transition states which lead to the four possible ortho-stereoisomers are shown above the reaction chromatograms. Background reaction: 2 mM diene and 70 mM dieneophile in a PBS solution for 24 hours at 298 K. DA_20_10 reaction: 50 µM protein, 0.5 mM diene, and 10 mM dieneophile in a PBS solution for 48 hours at 298K. The four stereoisomers were separated using liquid chromatography (11), and samples injected onto a Daicel AD-H column.

Figure 1:
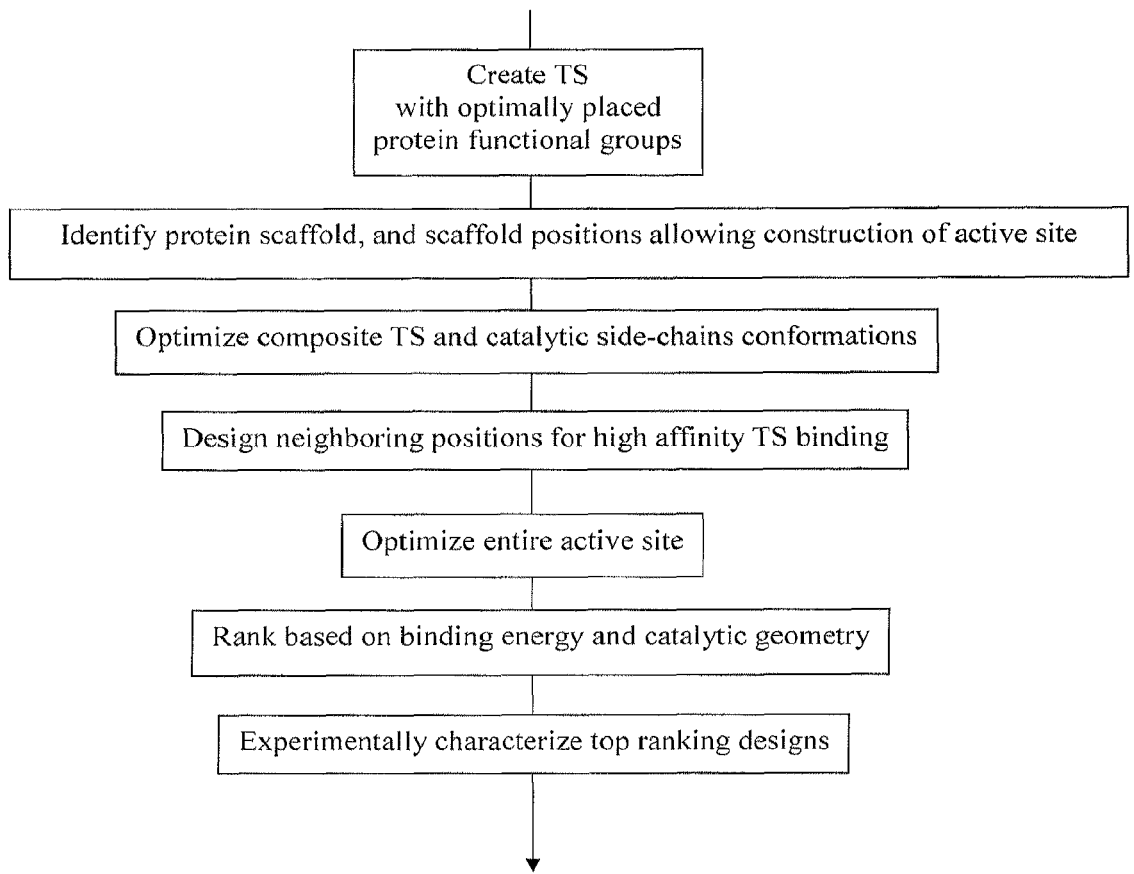
FIG. 1 illustrates the basic computational design methodology, including transition state design with catalytic functional groups, scaffold identification, followed by further design, and then optimization of the enzyme by targeted mutation and guided by functional assay.
Figure 19:
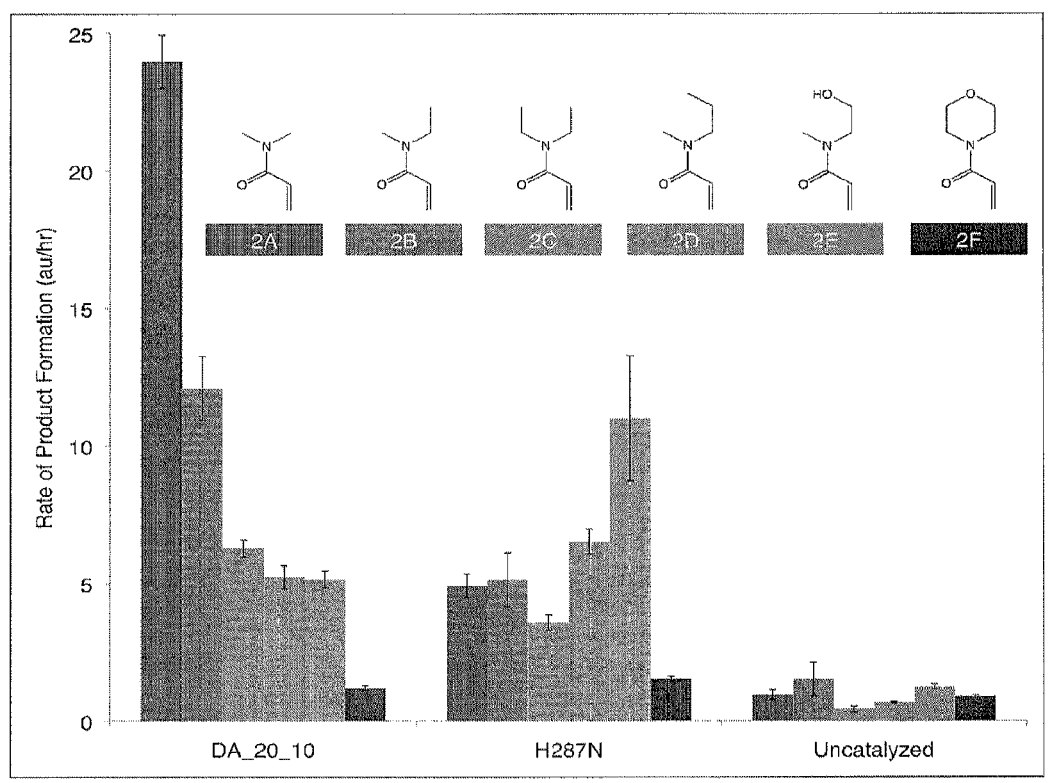

FIG. 19 illustrates the substrate specificity of DA_20_10 and a single mutant of DA_20_10, H287N. Reactions were carried out with 0.2 mM diene 1 (FIG. 1), and 10 mM of one of the six dienophiles depicted in PBS at 298K in the absence or presence of 60 µM DA_20_10 or DA_20_10_H287N. The depicted values in the figure are the mean (bars) and standard deviation (error bars) of four independent measurements of the product peak area (arbitrary units) formed per hour, determined using a liquid chromatography-mass spectroscopy assay. DA_20_10_H287N is most active on dienophile 2E, which is suboptimal for DA_20_10.

FIG. 20 shows the amino acid sequence (SEQ ID NO:9) for a second Diels-Alder enzyme catalyst, prepared from a ketosteroid isomerase scaffold. This enzyme also catalyzes the reaction illustrated in FIG. 2. Active site residues are shown in bold, and catalytic residues are indicated (in blue).

FIG. 21 illustrates exemplary reactions catalyzed by a Diels-Alder enzyme catalyst. Reaction (1) produces an intermediate used for the production of TAMIFLU. Reaction (2) leads to the production of a building block useful for the manufacture of the polymer PET. Reaction (3) can be used for the manufacture of vitamin B6. Reaction (4) is a reaction commonly referred to as "click chemistry."

DETAILED DESCRIPTION OF THE INVENTION

The Diels-Alder reaction generally takes place between a conjugated diene and a dienophile to produce a 1,4-addition product (with respect to the diene). The Diels-Alder reaction is a particular example of 4+2 sigmatropic cycloadditions. The term "dienophile" refers to a group or bond that is attracted to the diene. The reaction mechanism is a single step involving a cyclic redistribution of bonding electrons.

The reaction may be favored by the presence of electron-withdrawing groups on the dienophile, and by electron-donating groups on the diene. Frontier Orbital Theory shows that interaction of the highest occupied molecular orbital (HOMO) of the diene with the lowest unoccupied molecular orbital (LUMO) of the dienophile stabilizes the transition state and leads to charge transfer from diene to dienophile (30). Conversely, Frontier Orbital Theory also shows that a Diels-Alder reaction rate can be increased with the interaction of the lowest unoccupied molecular orbital (LUMO) of the diene with the highest occupied molecular orbital (HOMO) of the dienophile, leading to what is known as an inverse electron demand Diels-Alder reaction.

The interaction between the HOMO and LUMO, and the stability of the transition state relative to the ground state, may be increased by an electron donating effect to the diene (which increases the HOMO energy and stabilizes the positive charge accumulating in the transition state), and by an electron-withdrawing effect to the dienophile (which lowers the LUMO energy and stabilizes the negative charge accumulating in the transition state), or alternatively the converse for inverse electron demand reactions. Thus, any functional group from the protein side that will create or increase electron-withdrawing and electron-donating effects is predicted to increase the rate of the Diels-Alder reaction.

Alternatively or in addition, intramolecular and intermolecular Diels-Alder reaction rates may be enhanced by proximity effects, such as binding of the substrate or substrates into an enzyme active site so that the effective concentration of the substrate or substrates is higher than in water.

Figure 2:
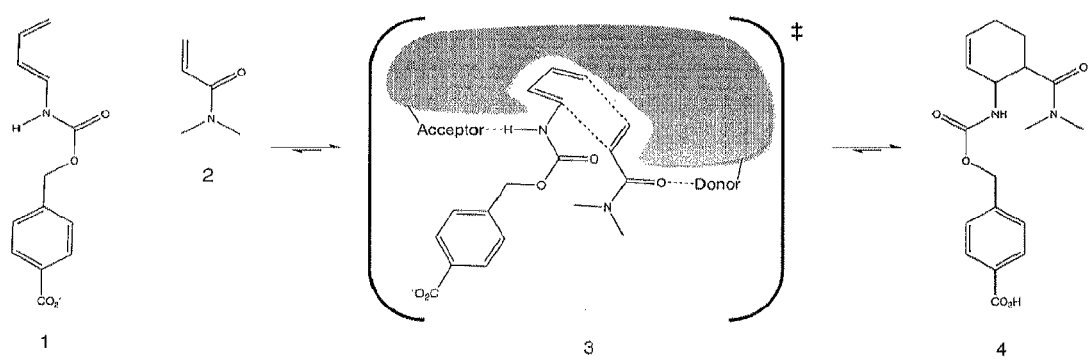
FIG. 2 illustrates a Diels-Alder reaction. Diene (1) and dienophile (2) undergo a pericyclic [4+2] cycloaddition (3) to form a chiral cyclohexene ring (4). Schematic of the design target active site, with hydrogen bond acceptor and donor groups activating the diene and dienophile and a hydrophobic pocket surrounding the reaction core, is depicted in (3).

As shown in FIG. 2, a hydrophobic binding pocket that binds the core of the two substrates in the optimal relative orientation with appropriately placed hydrogen bond donors and acceptors, is believed to be an effective Diels-Alder catalyst, because of both orbital and proximity effects.

Enzyme Structures and Scaffolds

In one aspect, the present invention provides enzyme catalysts for Diels-Alder reactions. The enzymes generally have scaffolds derived from non-immunoglobulin amino acid sequences. The scaffolds have active site "pockets" of sufficient size and shape to accommodate the desired Diels-Alder substrate(s). Exemplary scaffolds include diisopropylfluorophosphatase from *Loligo vulgaris* (and homologs thereof), which may generally be described as a 6-bladed beta barrel propeller scaffold (PDB-ID 1E1A), and ketosteroid isomerase from *Pseudomonas putida* (and homologs thereof), which may generally be described as a alpha+beta roll (PDB-ID 1OHO).

Figure 8:
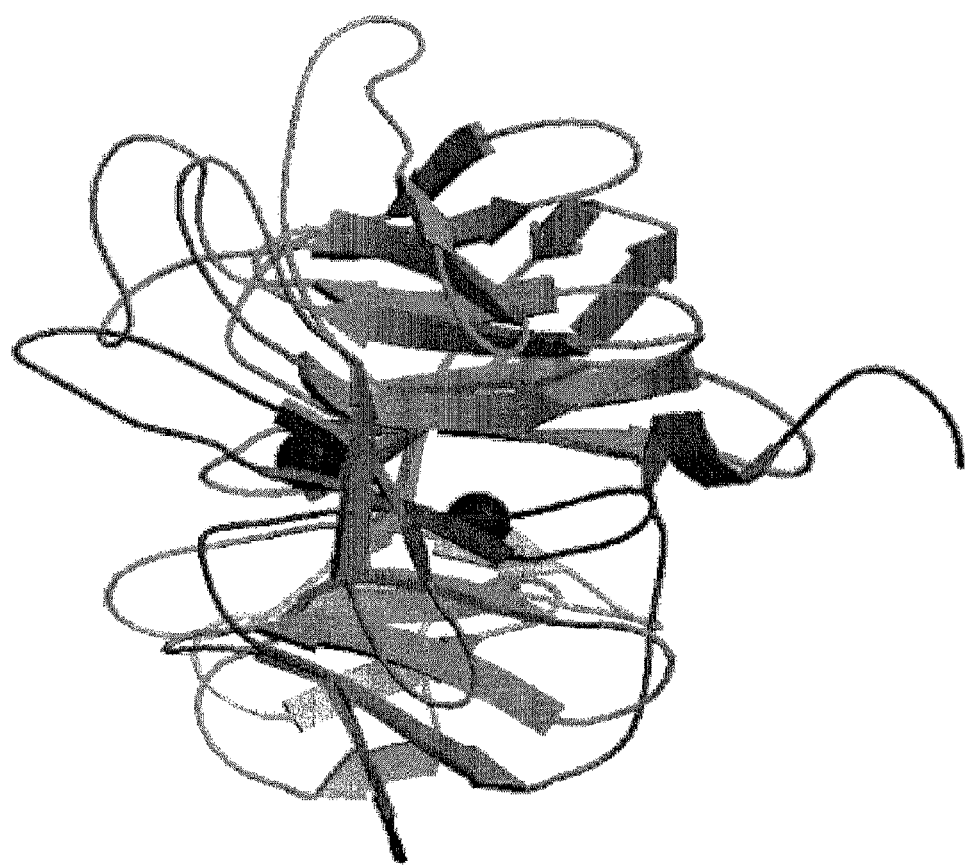
FIG. 8 illustrates the general structure of the scaffold. Diisopropylfluorophosphatase from *Loligo vulgaris* may generally be described as a 6-bladed beta barrel propeller scaffold (PDB-ID 1E1A).
Figure 9:
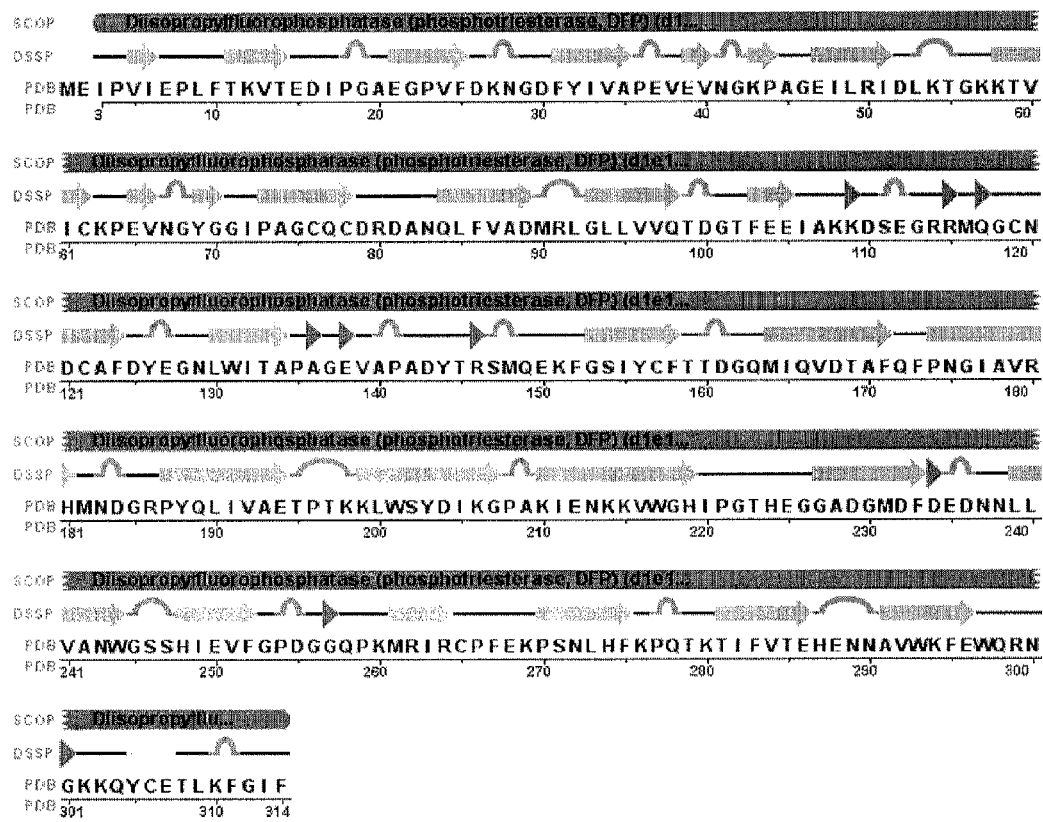
FIG. 9 shows the amino acid sequence of the scaffold with regional secondary structures. The scaffold contains about 51% beta-sheet (shown by arrows). Turns are also illustrated.

With respect to the diisopropylfluorophosphatase scaffold, the structure of the native scaffold is depicted in FIG. 8. The amino acid sequence for the native scaffold is provided herein as SEQ ID NO:2 (see FIGS. 7 and 9). In certain embodiments, the Diels-Alder catalysts of the invention are based upon this scaffold, with a Diels-Alder active site grafted onto the scaffold by mutation (e.g., substitution, deletion, and/or insertion of amino acid residues) as described in detail herein. The active site generally comprises amino acid side chains to act as electron-withdrawing and/or electron-donating groups to the Diels-Alder transition state. For example, the electron-withdrawing and electron-donating groups may be hydrogen bond donor and/or hydrogen bond acceptor groups in the proper orientation to stabilize a Diels-Alder transition state. In addition the Diels-Alder catalyst contains a substrate-binding pocket having a complementary interface of non-polar and/or polar amino acid residues to accommodate the Diels-Alder reaction. See FIG. 2.

The Diels-Alder catalyst may alternatively be based upon a homolog of the scaffold, including homologs of the scaffolds described in Table 1, and homologs of SEQ ID NO:2 and SEQ ID NO:9. The term "homolog" as used herein, includes both sequence homologs and structural homologs. For example, sequence homologs may be defined by a significant level of sequence identity or similarity between two sequences (e.g., between a particular scaffold and potential homolog). The level of identity or similarity can be determined using any suitable alignment tool known in the art, including Tatusova et al., *Blast 2 sequences—a new tool for comparing protein and nucleotide sequences, FEMS Microbiol Lett.* 174:247-250 (1999). In some embodiments, however, the homolog is a structural homolog, which may or may not exhibit detectable sequence identity or similarity with the scaffold of interest. Such structural homologs are protein sequences that share a very similar 3-dimensional tertiary structure. Structural homologs may be detected from structural databases by algorithms known as structural alignments. Examples of such programs that can be used to detect structural homologs include DALI/Dalillte (L. Holm and C. Sander (1996) *Science* 273(5275):595-60); Mammoth/Maxsub (D. Lupyan et al. (2005) *A new progressive-iterative algorithm for multiple structure alignment, Bioinformatics*), as well structurally annotated database such as SCOP (Andreeva et al. (2004), *SCOP database in* 2004: *refinements integrate structure and sequence family data, Nucleic Acids Res.* 32); and CATH (C. A. Orengo et al. (1997), *CATH—a hierarchic classification of protein domain structures, Structure* 5 (8): 1093-1108).

With respect to sequence homologs, the scaffold homologs or catalysts of the invention will have a level of identity to the scaffolds described herein of at least 20%, 30%, 40%, 50%, 60%, 70% 80%, 90%, 95%, or 98% (e.g., to SEQ ID NO:2, SEQ ID NO:9, or an enzyme disclosed in Table 1). With this level of homology, the enzyme maintains the basic tertiary fold of the scaffold and has Diels-Alder activity for a desired substrate (including substrates described herein), by mutation of active site residues. Alternatively, the scaffold homolog or catalyst is a structural homolog of a scaffold described herein, that is, the scaffold homolog or catalyst shares a similar 3-dimensional tertiary structure to the scaffolds described herein, as may be determined using the structural alignment tools described above.

In certain embodiments, the Diels-Alder catalyst has an active site comprising amino acid side chains positioned to stabilize a Diels-Alder transition state by electron-withdrawing effects of one or several hydrogen-bond donor(s) (interacting with the dienophile, or the diene in the case of inverse electron demand Diels-Alder reactions), and electron-donating effects of one or several hydrogen-bond acceptor(s) (interacting with the diene or dienophile). As demonstrated herein for an exemplary Diels-Alder reaction, the amino acid having a side chain accepting a hydrogen-bond from the transition state may be at the position corresponding to position 195 of SEQ ID NO:2. The amino acid having a side chain donating a hydrogen-bond to the transition state may be at the position corresponding to position 121 of SEQ ID NO:2.

Generally, any amino acid residue lining the active site, such as those described herein for SEQ ID NOS: 2 and 9, may carry functional side chains to provide electron withdrawing or electron donating effects to the Diels-Alder transition state. Such amino acids may be identified for a particular scaffold and with respect to a particular Diels-Alder transition state, using computational tools known in the art and described herein.

In certain embodiments, the amino acid at the position corresponding to position 195 of SEQ ID NO:2 has a side chain that is capable of stabilizing a Diels Alder transition state. For example, the amino acid residue at the position corresponding to position 195 of SEQ ID NO:2 may be any amino acid having a side chain capable of accepting a hydrogen bond from the diene, such as from a substituent of the diene containing a hydroxyl or NH group (e.g., carbamate NH). Exemplary diene substituents are described herein. In certain embodiments, the amino acid at the position corresponding to position 195 of SEQ ID NO:2 is asparagine or glutamine. The amino acid residue at the position corresponding to position 195 of SEQ ID NO:2 may be glutamine.

In these or other embodiments, the amino acid at the position corresponding to position 121 of SEQ ID NO:2 has a side chain capable of stabilizing a Diels-Alder transition state. Particularly, the amino acid residue at the position corresponding to position 121 of SEQ ID NO:2 may act as a hydrogen bond donor to an electron-withdrawing group of the dienophile. For example, the amino acid corresponding to position 121 of SEQ ID NO:2 may hydrogen bond with a substituent of the dienophile having the formula —C(O)R, where R is H or a substituent as described in greater detail herein. In certain embodiments, the amino acid at the position corresponding to position 121 of SEQ ID NO:2 is tyrosine, threonine, or serine. The amino acid residue at the position corresponding to position 121 of SEQ ID NO:2 may be tyrosine.

In still other embodiments, amino acid residues lining the pocket are designed to achieve hydrophobic packing, and hence rate enhancement through proximity effects of substrate binding, and without electron withdrawing/donating effects. For example, where the diene and/or dienophile have halogen substituents (e.g., Cl, Br, I), which essentially behave as hydrophobic moieties, hydrophobic packing around the transition state is predicted to provide rate enhancement through proximity effects.

The Diels-Alder enzyme catalyst, in addition to having the catalytic amino acid(s) on the protein scaffold in the proper position(s) to stabilize/bind the Diels-Alder transition state, also contains an active site pocket with a tight complementary surface to sufficiently accommodate, not only the desired substrate(s), but also the transition state and resulting product. For example, the active site may provide additional contacts to the substrate(s), and/or provide a complementary interface with the proper positioning of polar and non-polar amino acid side chains. The active site may be designed using any publicly available software, such as ROSSETTADESIGN. In some embodiments, the active site pocket is a relatively non-polar environment (e.g., hydrophobic), lined substantially with non-polar amino acids.

More particularly, amino acid residues lining the pocket (e.g., "active site residues") may be defined as amino acid residues whose C$\beta$ is within 8 Å of any atoms of the transition state structure, or whose C$\beta$ is within 10 Å of any such atoms but with a C$\alpha$-C$\beta$ vector pointing toward the transition state structure. In certain embodiments, such residues in the Diels-Alder catalyst are any hydrophobic or polar residue, excluding Gly and Pro (e.g., AILVYWFCMHQNST). Charged residues are allowed in positions in the scaffold where the same charge residue is present in the wild-type (or starting) structure. In certain embodiments, the pocket is lined with from about 3 to about 15 alanine residues, or from about 5 to about 10 alanine residues.

Amino acid residues that may carry catalytic side chains, may influence the position of the catalytic side chains, and/or influence the environment and/or shape of the active site include amino acid residues corresponding to positions 21, 36, 37, 39, 72, 74, 90, 120, 135, 136, 144, 146, 148, 149, 173, 175, 176, 196, 225, 229, 230, 244, 269, 271, 272 and 287 of SEQ ID NO:2.

With respect to an alternative enzyme design based upon the ketosteroid isomerase scaffold, amino acid residues that may carry catalytic side chains, or which may influence the position of the catalytic side chains, and/or which may influence the environment and/or shape of the active site include amino acid residues corresponding to positions 86, 93, 95, 121, 118, 116, 40, 43, 39, 84, 62, 59, 58, 37, 46, 55, 97, 114, 112, 99, 82, 19, 60, 64, 16, 31, 15, 80, 27, 56. of SEQ ID NO:9.

The Diels-Alder catalyzing enzyme may contain other amino acid substitutions that may be desirable for a particular Diels-Alder substrate or set of substrates, or which do not disrupt the shape of the active site or position of catalytic substrates. In certain embodiments, such additional amino acid substitutions do not significantly disrupt local secondary structures, as shown diagrammatically in FIG. 9 for the scaffold of SEQ ID NO:2. The effect of amino acid substitution, insertion, and/or deletion on the enzyme structure can be reasonably predicted with available computational tools, including ROSSETTADESIGN. The coordinates for the scaffolds are publicly available.

Thus, in various embodiments, the Diels-Alder catalyst has from about 5 to about 30 amino acid substitutions with respect to the scaffold (SEQ ID NO:2), and is capable of catalyzing a Diels-Alder reaction. In certain embodiments, the Diels-Alder catalyst has from about 10 to about 25, or from about 10 to about 20 amino acid substitutions with respect to SEQ ID NO:2. The Diels-Alder enzyme catalyst may also contain one or more amino acid insertions or deletions (e.g., collectively from about 1 to 30, 1 to 20, 1 to 10, or from about 1 to 5, e.g., 1, 2, or 3) with respect to the scaffold, so long as these insertions or deletions do not affect the overall integrity of the active site. For example, such insertions or deletions may be positioned at or near the N- and/or C-termini, to create truncated scaffolds and/or enzymes comprising the active site.

In certain embodiments, the Diels-Alder catalyst has the amino acid sequence of SEQ ID NO:4 (DA_20_00), or optionally with from 1 to about 10 amino acid substitutions, insertions, and/or deletions (collectively) with respect to SEQ ID NO:4. Generally, the Diels-Alder catalyst in accordance with these embodiments contains the catalytic residues at positions corresponding to positions 121 and 195 of SEQ ID NO:4, and otherwise has been modified in the substrate bonding pocket, to bind the Diels-Alder substrates of choice.

In certain embodiments, the Diels-Alder catalyst has the amino acid sequence of SEQ ID NO:6 (DA_20_04), or optionally with from 1 to about 10 amino acid substitutions, insertions, and/or deletions (collectively) with respect to SEQ ID NO:6. Generally, the Diels-Alder catalyst in accordance with these embodiments contains the catalytic residues at positions corresponding to positions 121 and 195 of SEQ ID NO:6, and otherwise has been modified in the substrate bonding pocket to bind the Diels-Alder substrates of choice.

In certain embodiments, the Diels-Alder catalyst has the amino acid sequence of SEQ ID NO:8 (DA_20_10), or optionally with from 1 to about 10 amino acid substitutions, insertions, and/or deletions (collectively) with respect to SEQ ID NO:8. The Diels-Alder catalyst in accordance with these embodiments contains the catalytic residues at positions corresponding to positions 121 and 195 of SEQ ID NO:8, and otherwise has been modified in the substrate bonding pocket to bind the Diels-Alder substrates of choice.

In other embodiments, the Diels-Alder catalyst has the amino acid sequence of SEQ ID NO:9, or optionally with from 1 to about 20, or 1 to about 10 amino acid substitutions, insertions, and/or deletions (collectively) with respect to SEQ ID NO:9. The Diels-Alder catalyst in accordance with these embodiments may be modified in the substrate binding pocket to bind the Diels-Alder substrates of choice.

The Diels-Alder catalyst may be designed to stabilize the transition state for a variety of Diels-Alder reactants. That is, amino acid substitutions, insertions and/or deletions with respect to the scaffold, or with respect to the Diels-Alder catalyzing enzymes of SEQ ID NOS: 4, 6, 8, or 9 may be selected with regard to a particular Diels-Alder reaction.

In various embodiments, the enzyme catalyzes a reaction with a linear or cyclic diene. Where cyclic, the diene may be a five- or six-membered ring having two conjugated double bonds, and the ring may have multiple heteroatoms (typically 1 or 2), such as N, O, and/or S. Generally, the diene must not be covalently locked into the trans conformation, so as to support the Diels-Alder reaction.

The diene may be substituted, for example, with up to four substituents. The identity of the substituents will depend on the desired product, as well as the anticipated catalytic mechanism. Exemplary diene substituents have less than about 30, about 20, or about 15 atoms, and may contain one or more (e.g., 1-10) heteroatoms selected from O, N, and/or S. Exemplary dienes may have substituents independently selected from halogen (e.g., independently selected from Cl, Br, Fl, I), haloalkyl, alkyl (e.g., C1-C5), —C(O)O, —C(O) OR, —COR, —CN, —C(R)N, —CH(O), —C(O)—, aryl (e.g., substituted or unsubstituted phenyl), OH and —OR. R may be any group, for example, containing about 20 or fewer atoms (e.g., 10 or fewer atoms). For example, R may represent a hydrogen or a carbon-containing substituent such as C1-5 alkyl (e.g., methyl), and may optionally include one or more (e.g., 1-3) heteroatoms independently selected from O, N, or S.

In certain embodiments, at least one substituent is an electron-donating group, which favors the Diels-Alder reaction, and which may interact with the Diels-Alder enzyme catalyst to stabilize the Diels-Alder transition state. For example, the diene may have a substituent defined by —N(H)R, or a substituent allowing for a similar hydrogen-bonding geometry with the hydrogen bond acceptor as exemplified by the position corresponding to position 195 of SEQ ID NO:2 (e.g., Q195). R may be as defined above, or as described elsewhere herein. Conversely, in the case of inverse-electron demand Diels-Alder reactions, at least one substituent is an electron-withdrawing group.

The dienophile may also be substituted, and the identity of such substituents will depend on the desired product as well as the intended catalytic mechanism. The dienophile in various embodiments is substituted with one or more electron-withdrawing groups, making the dienophile more electrophilic. The dienophile may be linear or cyclic, and generally includes an alkene or alkyne. The substituent may be any group having less than about 30, about 20, or about 15 atoms, and may be suitable for withdrawing electron density from the carbon-carbon double or triple bond. The electron-withdrawing group may contain one or more (e.g., 1-5) heteroatoms including O, N, and/or S. In embodiments corresponding to inverse electron demand Diels Alder reactions, the dienophile may be substituted with one or more electron-donating groups. An electron-donating group may contain one or more (e.g., 1-5) heteroatoms including O, N, and/or S.

In certain embodiments, the dienophile has one or more substituents independently selected from halogen (e.g., independently selected from Cl, Br, Fl, I), haloalkyl, —C(O)OR, —COR, —CN, —C(R)N, —CH(O), —C(O)—, aryl (e.g., substituted or unsubstituted phenyl), OH and OR. R may be any group, for example, containing about 20 or fewer atoms (e.g., 10 or fewer) and supporting the electron-withdrawing capacity of the overall substituent. For example, R may represent a hydrogen or a carbon-containing substituent such as C1-5 alkyl (e.g., methyl), and may optionally include one or more (e.g., 1-3) heteroatoms independently selected from O, N, or S.

In some embodiments, the dienophile has a substituent defined by —C(O)R, where R is H, linear or branched alkyl (e.g., C1-C5), or N(R)$_2$. Alternatively, the dienophile may have a substituent allowing for a similar hydrogen-bonding geometry with a hydrogen-bond donor at position 121 (e.g., Y121) of the Diels-Alder enzyme catalyst.

In some embodiments, the dienophile is a substituted or unsubstituted C1-4 alkene, such as ethene or ethyne, 1,2 di-chloroethene or 2-buten-1,4-ol as shown in FIG. 21.

The dienophile may be a di-substituted alkene or alkyne, and may be in either cis or trans configuration. The stereochemistry of the dienophile will be maintained in the resulting product.

Generally, the Diels-Alder catalyst is designed to provide the desired stereochemistry. In making the stereo-selective enzyme, the substrates providing the desired stereochemistry for the resulting Diels-Alder product are first selected for active site design or optimization. While there can be regio-, diastereo-, but not enantioselectivity in the uncatalyzed reaction, the present application shows that the Diels-Alder catalyzing enzyme is regio, diastereo, and enantioselective, and that stereoselectivity can be controlled by the enzyme. The exemplified designs are based on one diastereo and one enantiomer of the Diels-Alder reaction between 4-carboxybenzyl trans-1,3-butadiene-1-carbamate and N,N-dimethylacrylamide; namely, an endo 3R4S isomer. Enzymes may be designed to catalyze products with alternative stereochemistry.

The Diels-Alder catalyzing enzyme may produce various products, such as products illustrated in FIG. 21, with or without introduction of chiral centers. For example, reaction (1) produces an intermediate used for the synthesis of TAMIFLU, where the active is one of 32 possible stereoisomers. For this reaction, the Diels-Alder enzyme may provide tight hydrophobic binding of 1,2-dichloro ethene, together with H-bonding of the hydroxyl group on C4 of the diene, and charged H-bonding with the carboxylate moiety on the C2 of the diene. Reaction (2) is a Diels-Alder reaction that leads to one of the building blocks used for the manufacture of the polymer PET. This reaction does not introduce any chiral center (no stereoselectivity). For this reaction, the diene may be positioned, and the transition state stabilized, by making hydrogen bonds to the carboxylate and hydroxyl substituents. Reactions (3) and (4) are examples of hetero Diels-Alder reactions. Reaction (3) is a Diels-Alder reaction to manufacture vitamin B6. No enzyme exists in nature that catalyzes such a Diels-Alder reaction. The current synthetic industrial route uses high temperature (around 200° C.) and inorganic catalysts. For this reaction, the diene may be positioned, and the transition state stabilized, by making hydrogen bonds to the carboxylate and hydroxyl substituents. Reaction (4) represents what is commonly known as "click chemistry". With R being variable, this bimolecular reaction can be used to generate libraries of compounds, e.g., for combinatorial chemistry. The reaction introduces chiral centers and thus it would be extremely beneficial to control the stereoselectivity with a custom-designed enzyme. Furthermore, the usage of custom-designed enzymes would remove the need to use copper catalysts. A strategy similar to that for reactions 2 and 3 may be used to stabilize the transition state for reaction 4 depending on the substituent R.

Methods of Making Diels-Alder Enzyme Catalysts

In other aspects, the invention provides methods for making enzymes that catalyze Diels-Alder reactions. The methods may involve de novo enzyme design by transition state, substrate or product placement within a scaffold or scaffold library, or in other embodiments, the methods involve designing the scaffolds and Diels-Alder enzymes described herein (SEQ ID NOS:2, 4, 6, 8, 9), and homologs thereof, for desired substrates.

For de novo enzyme design, the method comprises first identifying functional reactive sites (e.g., substrate binding residues) required to promote the desired Diels-Alder reaction; followed by the use of hashing algorithms to identify potential protein backbone structures (i.e., scaffolds) capable of supporting the required functional sites. An algorithm (e.g. ROSETTADESIGN) is then employed to computationally develop a plurality of different protein sequences that accommodate the identified scaffolds. Computational ranking is performed to identify a relatively small number of potential enzyme designs, which can be empirically tested for the desired enzymatic efficiency. Potential candidates are then assayed experimentally. After experimental assay, designs can be further improved using in vitro evolution to identify more efficient variants. The method is summarized diagrammatically in FIG. 1.

The basic methods for de novo enzyme design have been described in Zanghellini et al., *New Algorithms and an in silico Benchmark for Computational Enzyme Design, Protein Science* 15:2785-2794 (2006); as well as WO 2009/076655, each of which is hereby incorporated by reference in its entirety.

First, a Diels-Alder active site model, comprising a transition state model and/or substrate(s) and/or product model(s) is created computationally with proper positioning of catalytic functional groups. As discussed, the Diels-Alder reaction mechanism is a single step involving a cyclic redistribution of bonding electrons. Frontier Orbital Theory shows that interaction of the highest occupied molecular orbital (HOMO) of the diene with the lowest unoccupied molecular orbital (LUMO) of the dienophile stabilizes the transition state and leads to charge transfer from diene to dienophile (30). The reverse is also possible, and called inverse electron demand Diels-Alder reaction (as described elsewhere herein). The interaction between the HOMO and LUMO, and the stability of the transition state relative to the ground state, may be increased by a hydrogen bond acceptor interacting with the diene (to increase the HOMO energy and stabilize the positive charge accumulating in the transition state), and by a hydrogen bond donor interacting with an electron-withdrawing group of the dienophile (which lowers the LUMO energy and stabilizes the negative charge accumulating in the transition state), while the reverse is done for an inverse-electron demand Diels-Alder reaction. As shown in FIG. 2, a hydrophobic binding pocket that binds the core of the two substrates in the optimal relative orientation with appropriately placed hydrogen bond donors and acceptors, is believed to be an effective Diels-Alder catalyst. Thus, the transition state model may be stabilized by substituent effects as described and/or by proximity effects, where substrates are bound in the proper position for catalysis.

The reactants or groups that make up the transition state generally will include a conjugated diene, and an alkene or alkyne, although the precise substrates may vary.

The diene may be a linear or cyclic diene. Where cyclic, the diene may be, for example, a five- or six-membered ring having two conjugated double bonds. The diene may have, for example, one or more heteroatoms, such N, O, and/or S. Generally, the diene must exist at least partially in the cis configuration, so as to support the Diels-Alder reaction.

The diene may be substituted with one or more substituents, the identity of which will depend on the desired product and desired catalytic mechanism. Exemplary diene substituents have less than about 50, about 30, about 20, or about 15 atoms, and may contain one or more (e.g., 1-5) heteroatoms selected from O, N, or S, so long as such substituents do not interfere with the Diels-Alder reaction. In certain embodiments, at least one substituent is capable of donating or accepting a hydrogen bond or has a polar group that can interact with the enzyme active site, thereby stabilizing the Diels-Alder transition state. For example, at least one substituent may be halogen (e.g., independently selected from Cl, Br, Fl, I), haloalkyl, alkyl (e.g., C 1-C5), —C(O)O, —C(O)OR, —COR, —CN, —C(R)N, —CH(O), —C(O)—, aryl (e.g., substituted or unsubstituted phenyl), OH, or —OR. R may be any group, for example, containing about 20 or fewer atoms (e.g., 10 or fewer atoms). For example, R may represent a hydrogen or a carbon-containing substituent such as C1-5 alkyl (e.g., methyl), and may optionally include one or more (e.g., 1-3) heteroatoms independently selected from O, N, or S.

In certain embodiments, the diene has a substituent defined by —N(H)R, or a substituent that provides for a similar hydrogen-bonding geometry. R may be as defined above, or as described elsewhere herein.

The dienophile may be substituted or unsubstituted, and the identity of such substituents will depend on the desired product and desired catalytic mechanism. The dienophile in various embodiments is substituted with at least one electron-withdrawing group, making the dienophile more electrophilic. The dienophile may be linear or cyclic, and generally includes an alkene or alkyne. The dienophile may also have one or more heteroatoms selected from O, N, and/or S. The substituent may be any group having less than about 30, about 20, or about 15 atoms, and may be suitable for withdrawing electron density from the carbon-carbon double or triple bond. The electron-withdrawing group may contain one or more (e.g., 1-5) heteroatoms selected from O, N, or S.

In certain embodiments, the diene has at least one substituent selected from halogen (e.g., independently selected from Cl, Br, Fl, I), haloalkyl, —C(O)OR, —COR, —CN, —C(R) N, —CH(O), —C(O)—, aryl (e.g., substituted or unsubstituted phenyl), OH, and OR. R may be any group, for example, containing about 30 or fewer, or 20 or fewer atoms (e.g., 10 or fewer). For example, R may represent a hydrogen or a carbon-containing substituent such as C1-5 alkyl (e.g., methyl), and may optionally include one or more (e.g., 1-3) heteroatoms independently selected from O, N, or S.

In some embodiments, the dienophile has a substituent defined by —C(O)R, where R is H, linear or branched alkyl (e.g., C1-C5), or $N(R)_2$. Alternatively, the substituent provides for a similar hydrogen-bonding geometry as the C(O)R diene substituent described herein.

In some embodiments, the dienophile is a substituted or unsubstituted C1-4 alkene, such as ethene or ethyne, 1,2 di-chloroethene or 2-buten-1,4-ol as shown in FIG. 21.

Generally, the transition state and placement of substrate(s) and product(s) in the active site model will be designed to account for the desired stereochemistry. The transition state may be derived from the Diels-Alder reactants illustrated in FIG. 21.

Figure 4A:
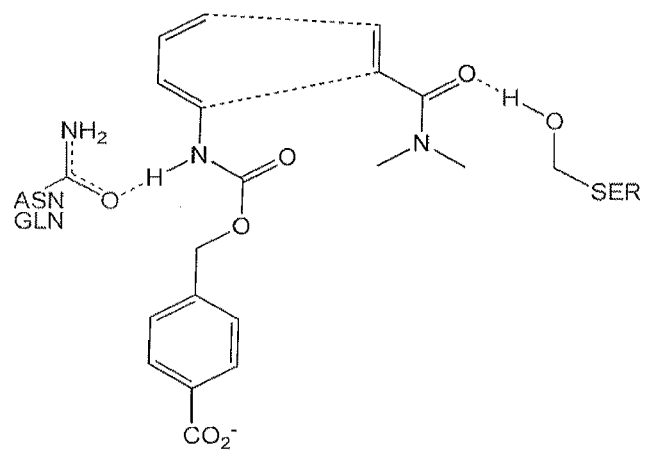
FIG. 4A shows the first minimal active site used for design. The two catalytic residues are an Asparagine/Glutamine as a hydrogen bond acceptor on the carbamate nitrogen, and a Serine as a hydrogen bond donor to the diene carbonyl. The final minimal active site contains a consensus between the substrate, transition state and product structures, but only a symbolic representation of the transition state structure is represented here.
Figure 4B:
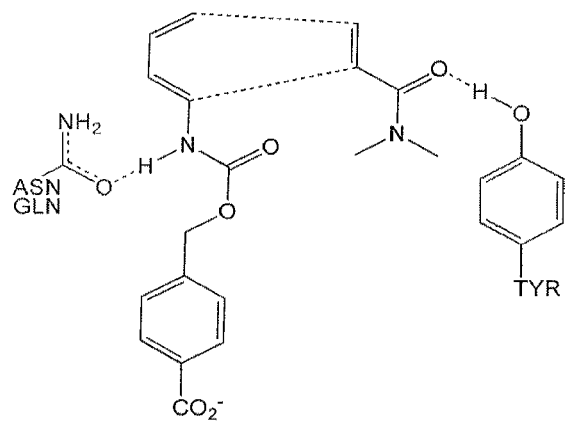
FIG. 4B shows the second minimal active site used for design. The two catalytic residues are an Asparagine/Glutamine as a hydrogen bond acceptor on the carbamate nitrogen, and a Tyrosine as a hydrogen bond donor to the diene carbonyl. The final minimal active site contains a consensus between the substrate, transition state and product structures, but only a symbolic representation of the transition state structure is represented here.

A transition state for an exemplary Diels-Alder reaction is shown in FIG. 4, with asparagine or glutamine hydrogen bond acceptor to a diene substituent (NH carbamate), and a serine or tyrosine as a hydrogen bond donor to a carbonyl of the dienophile. The diene and dienophile substituents shown may be replaced with any substituent described herein, where such substituents allow for stabilization of the transition state through interaction with amino acid functional groups (e.g., hydrogen bonding, electrostatic interaction, and van der waals and hydrophobic interactions).

A protein scaffold is then identified that could support the active site model (e.g., transition state, substrate(s), and/or product(s)) with desired catalytic functional groups. Generally, the method employs a hashing algorithm, as described in Zanghellini et al., *New Algorithms and an in silico Benchmark for Computational Enzyme Design, Protein Science* 15:2785-2794 (2006); as well as WO 2009/076655, each of which is hereby incorporated by reference in its entirety.

In the first hashing method, an inverse rotamer tree approach is used with a modified version of a known geometric hashing algorithm (Bachar et al. 1993), to find positions in a set of scaffolds that can support the catalytic site. In the second hashing method, based on iterative side chain placement and hashing in six-dimensional space, candidate catalytic sites in scaffolds are detected in linear time. Both methods are followed by the design of the pocket using the Rosetta design methodology.

More particularly, in the first hashing technique, (also referred to as the "inside-out" method), an inverse rotamer tree is built up from the active site description, and the backbone coordinates of all the rotamer combinations are compared to backbone coordinates of the set of scaffolds using a geometric-hashing based algorithm. In the second, "outside-in" hashing method, side chain rotamers and the transition state (TS) model are sequentially placed at all scaffold positions, and the position of the TS model is recorded in a hash table. The hash table is then scanned for TS positions that are found when placing each of the catalytic side chains independently. These positions represent sites in the scaffolds where the specified active site can be successfully constructed.

The idea of the inverse rotamer tree (the first hashing technique noted above) is to convert the description of the active site in terms of functional groups into a description in terms of protein backbone coordinates, which can then be used to search a set of protein scaffolds, or to guide de novo scaffold design. This technique is the inverse of the standard side chain packing problem, in which the positions of the backbone coordinates are known. The algorithm employs a standard rotameric description of the side chains to solve the problem (Dunbrack and Cohen 1997); but, rather than building outward from the backbone coordinates, the side chains are grown backward from the functional group positions that are placed around the TS model in positions optimal for catalytic functionality. This approach generates an inverse rotamer tree specifying the possible placements of the protein backbone around the TS model that are compatible with the specified active site, in the sense that the relevant amino acids can be placed to achieve the desired active site geometry.

Once the inverse rotamer tree has been built, each combination of backbone coordinates for the catalytic residues is searched against a set of scaffolds (a step subsequently referred to as matching) using a hashing-based approach. A set of scaffolds for matching may include a plurality of scaffolds described in Table 1, or sequence and/or structural homologs thereof. In some embodiments, the set of scaffolds comprises at least 5, 10, 20, 100, or more of such scaffolds.

TABLE 1

Overview of protein scaffold set

| PDP code | resolution (Å) | protein name | co-crystallized ligand |
|---|---|---|---|
| 148l | 1.90 | T4 Lysozyme | N/A |
| 1a53 | 2.00 | Indole-3-Glycerolphophate Synthase | Indole-3-Glycerol Phosphate |
| 1abe | 1.70 | L-Arabinose Binding Protein | N/A |
| 1b9b | 2.85 | Triosephosphate Isomerase | N/A |
| 1btm | 2.80 | Triosephosphate Isomerase | 2-Phosphoglycolic Acid |
| 1c2t | 2.10 | Glycinamide Ribonucleotide Transformylase | Glycinamide Ribonucleotide |
| 1c9u | 2.20 | Quinoprotein Glucose Dehydrogenase | Pyrroloquinoline Quninone |
| 1cbs | 1.80 | Retinoic Acid Binding Protein Ii | Retinoic Acid |
| 1cq1 | 1.90 | Quinoprotein Glucose Dehydrogenase | Pyrroloquinoline Quinone |
| 1cru | 1.50 | Quinoprotein Glucose Dehydrogenase | Pyrroloquinoline Quinone |
| 1crz | 1.95 | Tolb Protein | N/A |
| 1dc9 | 2.10 | Fatty Acid Binding Protein | N/A |
| 1dl3 | 2.70 | Phosphoribosylantranilate Isomerase | N/A |
| 1dqx | 2.40 | 5'-Phosphate Decarboxylase | 6-Hydroxyuridine-5'-Phosphate |
| 1e1a | 1.80 | Diisopropyl-fluorophosphatase | N/A |
| 1e2r | 1.59 | Cytochrome Cd1 Nitrite Reductase | N/A |
| 1ebg | 2.10 | Enolase | Phosphonoacetohydroxamic Acid |
| 1ecm | 2.20 | Chorismate Mutase | 8-Hydroxy-2-Oxabicyclo[3.3.1]Non-6-Ene-3,5-Dicarboxylic Acid |
| 1eix | 2.50 | Orotidine 5'-Monophosphate Decarboxylase | 1-(5'-Phosphate-Beta-D-Ribofuranosyl)Barbituric Acid |
| 1eux | 2.10 | Thiol Protease | (2s,3s)-3-(1-(N-(3-Methylbutyl) Amino)-Leucylcarboxyl) Oxirane-2-Carboxylate |
| 1ey4 | 1.60 | Staphylococcal Nuclease | N/A |
| 1f5j | 1.80 | Beta-1,4-Xylanase | N/A |
| 1fkj | 1.70 | Fk506 Binding Protein | 8-Deethyl-8-[But-3-Enyl]-Ascomycin |
| 1ftx | 2.20 | Alanine Racemase | (1s)-1-[((1e)-{3-Hydroxy-2-Methyl-5-[(Phosphonooxy)Methyl]Pyridin-4-Yl}Methylene)Amino]Ethylphosphonic Acid |
| 1gca | 1.70 | Glucose/Galactose Binding Protein | Beta-D-Galactose |
| 1gci | 0.78 | Subtilisin | N/A |
| 1gqv | 0.98 | Eosinophil-Derived Neurotoxin | N/A |

TABLE 1-continued

Overview of protein scaffold set

| PDP code | resolution (Å) | protein name | co-crystallized ligand |
|---|---|---|---|
| 1gye | 2.50 | Arabian Endo-1,5-Alpha-L-Arabinosidase | N/A |
| 1h1a | 1.75 | Endoxylanase | N/A |
| 1h2j | 1.15 | Endoglucanase | 2,4-Dinitrophenyl-2-Deoxy-2-Fluoro-Beta-D-Cellobioside |
| 1h61 | 1.40 | Pentaerythritol Tetranitrate Reductase | Flavin Mononucleotide |
| 1h6l | 1.80 | Phytase | N/A |
| 1hsl | 1.89 | Histidine-Binding Protein | Histidine |
| 1i4n | 2.50 | Indole-3-Glycerol Phosphate Synthase | N/A |
| 1icm | 1.50 | Fatty Acid Binding Protein | Myristic Acid |
| 1icn | 1.74 | Fatty Acid Binding Protein | Oleic Acid |
| 1ifc | 1.19 | Fatty Acid Binding Protein | N/A |
| 1igs | 2.00 | Indole-3-Glycerolphosphate Synthase | N/A |
| 1jcl | 1.05 | Deoxyribose Phosphate Aldolase | 1-Hydrox-Pentane-3,4-Diol-5-Phosphate |
| 1lbf | 2.05 | Indole-3-Glycerol Phosphate Synthase | 1-(O-Carboxy-Phenylamino)-1-Deoxy-D-Ribulose-5-Phosphate |
| 1lbl | 2.40 | Indole-3-Glycerol Phosphate Synthase | 1-(O-Carboxy-Phenylamino)-1-Deoxy-D-Ribulose-5-Phosphate |
| 1lbm | 2.80 | Phosphoribosyl Anthranilate Isomerase | 1-(O-Carboxy-Phenylamino)-1-Deoxy-D-Ribulose-5-Phosphate |
| 1lic | 1.60 | Lipid Binding Protein | 1-Hexadecanosulfonic Acid |
| 1m4w | 2.10 | Endoxylanase | N/A |
| 1mbt | 3.00 | Uridine Diphospho-N-Acetylenolpyruvyl-glucosamine Reductase | N/A |
| 1n1s | 1.64 | Sialidase | N/A |
| 1n1t | 1.60 | Sialidase | 2-Deoxy-2,3-Dehydro-N-Acetyl-Neuraminic Acid |
| 1n1v | 2.10 | Sialidase | 2-Deoxy-2,3-Dehydro-N-Acetyl-Neuraminic Acid |
| 1n1y | 2.80 | Sialidase | O-Sialic Acid |
| 1ney | 1.20 | Triosephosphate Isomerase | 1,3-Dihydroxyacetonephosphate |
| 1oex | 1.10 | Endothiapepsin | N/A |
| 1oho | 1.90 | Steroid Delta-Isomerase | Equilenin |
| 1ov7 | 2.00 | Lysozyme | 2-Allyl-6-Methyl-Phenol |
| 1ovk | 2.10 | Lysozyme | N-Allyl-Aniline |
| 1p6o | 1.14 | Cytosine Deaminase | 4-Hydroxy-3,4-Dihydro-1h-Pyrimidin-2-One |
| 1pii | 2.00 | N-(5'phosphoribosyl) Anthranilate Isomerase | N/A |
| 1poo | 2.10 | Phytase | N/A |
| 1pt2 | 2.00 | Transforming Protein P21/H-Ras- | Phosphoaminophosphonic Acid-Guanylate Ester |
| 1pvx | 1.59 | Endo-1,4-Beta Xylanase | N/A |
| 1q7f | 1.95 | Brain Tumor Ccg10719-Pa | N/A |
| 1qo2 | 1.85 | N-((5-Phosphoribosyl)-Formimino)-5-Aminoimidazol-4-Carboxamid Ribonucleotid Isomerase | N/A |
| 1rx8 | 2.80 | Dihydrofolate Reductase | NADP Nicotinamide-Adenine-Dinucleotide Phosphate |
| 1s1d | 1.60 | Apyrase | Phosphomethylphosphonic Acid Guanosyl Ester |
| 1sjw | 1.35 | Nogalonic Acid Methyl Ester Cyclase | Methyl 5,7-Dihydroxy-2-Methyl-4,6,11-Trioxo-3,4,6,11-Tetrahydrotetracene-1-Carboxylate |
| 1sq9 | 1.90 | Antiviral Protein Ski8 | N/A |
| 1st8 | 2.35 | Frucan 1-Exohydrolase Iia | N/A |
| 1suu | 1.75 | Dna Gyrase Subunit A | N/A |
| 1thf | 1.45 | Hisf Protein | N/A |
| 1tml | 1.80 | Endo-1,4-Beta-D-Glucanase | N/A |
| 1tsn | 2.20 | Thymidylate Synthase | 5-Methyl-5,6,7,8-Tetrahydrofolic Acid |
| 1uyp | 1.90 | Beta-Fructosidase | Citric Acid |
| 1v04 | 2.20 | Serum Paraoxonase/Arylesterase 1 | N/A |
| 1w8n | 2.10 | Sialidase | 2-Deoxy-2,3-Dehydro-N-Acetyl-Neuraminic Acid |
| 1w8o | 1.70 | Sialidasae | Lactose |
| 1wdn | 1.94 | Glutamine Binding Protein | Glutamine |
| 1yna | 1.55 | Endo-1,4-Beta-Xylanase | N/A |
| 2btm | 2.40 | Triosephosphate Isomerase | 2-Phosphoglycolic Acid |

TABLE 1-continued

Overview of protein scaffold set

| PDP code | resolution (Å) | protein name | co-crystallized ligand |
|---|---|---|---|
| 2dri | 1.60 | D-Ribose-Binding Protein | Ribose |
| 2fhr | 2.20 | Sialidase | 5-(Acetylamino)-2,6-Anhydro-3,5-Dideoxy-3-Fluorononic Acid |
| 2fp9 | 2.96 | Strictosidine Synthase | D(−)-Tartaric Acid |
| 2fpc | 3.00 | Strictosidine Synthase | Methyl (2s,3r,4s)-2-(Beta-D-Glucopyranosyloxy)-4-(2-Oxoethyl)-3-Vinyl-3,4-Dihydro-2h-Pyran-5-Carboxylate |
| 2h13 | 1.58 | Wd-Repeat Protein | N/A |
| 2ifb | 2.00 | Fatty Acid Binding Protein | Palmitic Acid |
| 2izj | 1.30 | Streptavidin | Biotin |
| 3vgc | 1.67 | Chymotrypsin | L-1-Naphthyl-2-Acetamido-Ethane Boronic Acid |
| 4fua | 2.43 | L-Fuculose-1-Phosphate Aldolase | Phosphoglycolohydroxamic Acid |
| 6cpa | 2.00 | Carboxypeptidase A | O-(((1r)-((N-Phenylmethoxycarbonyl-L-Alanyl)Amino)Ethyl)Hydroxyphosphono)-L-Benzylacetic Acid |

Given the set of scaffolds to be searched, the first hashing algorithm begins by building a multiple key hash table. The backbone coordinates (e.g., N, Ca, C) for each pair of residues for each scaffold are mapped onto a unique key that is computed from the Ca-Cb distance and the [Ca, Cb] vector orientations. For enhanced speed, all the scaffolds are mapped into a single hash in memory at the beginning of the program. Each combination of backbone atom coordinates from the inverse rotamer tree is matched against the backbone distances and orientations stored in the hash table using a subgraph isomorphism algorithm similar to that described by Russell (1998). Matches are ranked based on their structural similarity (in RMSD) to the specified active site geometry and the absence of atomic clashes between the TS model, the placed catalytic side chains, and the protein backbone.

The idea of this approach is to build forward from the protein backbone to the TS model for each catalytic side chain independently, and then to identify TS placements compatible with placement of each catalytic residue. The method includes ligand orientation, as well as center of mass coordinates. The following first describes the storage of the position of the TS model for each catalytic side chain rotamer placed at each position using a hash table and next, the processing of the hash table to extract sets of positions compatible with the specified active site geometry. Finally, performance enhancements to the method using pre-computed grids to restrict TS placement to clefts and pockets in the scaffolds, and to speed up the evaluation of atomic clashes with the protein backbone are discussed.

Figure 5:
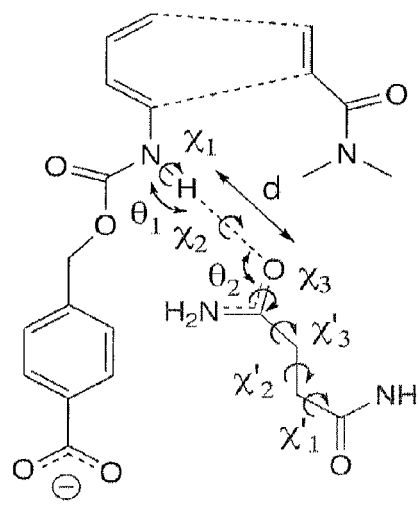
FIG. 5 shows the geometrical parameters used to place the first catalytic side-chain functional group in active site descriptions. The idealized geometries are listed, as well as the deviation (tolerance) used both for generating the discrete ensemble of rigid-body placements of transition state consensus structures, and for defining the constraint energy for minimization.

For each protein scaffold, a set of potential active site positions is predefined, either all positions in the protein, or positions lining cavities or small molecule binding sites. For each amino acid residue in the catalytic site description, all rotamers from the Dunbrack backbone dependent library are placed at each position. If there is no clash with the protein backbone, the TS model for the reaction is positioned as specified in the catalytic site definition. For catalytic side chain-TS interactions such as hydrogen bonds, where there are many chemically equivalent interaction geometries, a large set of TS model placements are considered; the fineness of the sampling around the varying degrees of freedom is illustrated in FIG. 5.

Empirical testing is performed to build and test the actual enzymatic activity of selected sequences. If desired, those sequences showing promise are further manipulated using the technique of in vitro evolution, and the results are then empirically tested.

The TS model and the catalytic side chains are refined to eliminate clashes and optimize the catalytic geometry. Then, the identity and conformations of amino acid residues located near the active site are optimized using a software module referred to as ROSETTADESIGN. Finally, the designs are ranked based on the computed TS binding energy, considering only designs where the catalytic constraints are satisfied. However, it should be emphasized that determination of the catalytic efficacy of a design requires experimental characterization.

To focus the design calculations on promising regions of the scaffold, the center of mass of the TS model may be restricted to clefts or pockets that are likely to be large enough to comprise a viable active site. A square grid box is first constructed that covers the regions targeted for active site design. This grid is then trimmed to remove all the grid points that are <2.25 Å from any protein backbone atom. Any residue on the protein backbone that has a Ca-Cb vector pointing toward one of those grid points and a Ca <3.5 Å from any grid point is then included in the set of active site positions. In practice, the use of the grid does not substantially reduce the number of matches found, but it considerably speeds up the search process by eliminating regions unlikely to contribute high ranking active site designs.

To speed up the evaluation of clashes between the TS model and the protein backbone, a "backbone" grid is constructed that contains points that are <2.25 Å from any backbone atom. TS model placements for which atoms overlap the backbone grid are not included in the hash.

For each match found with the inverse rotamer tree or the ROSETTAMATCH method, residues around the TS model, other than the catalytic residues, are truncated to glycines or alanines. In certain embodiments, the modification of truncation to alanine (Ala), which may result in enzymes that are easier to handle.

The initial placements of the TS model and catalytic side chain conformations are optimized by rigid body minimization followed by side chain minimization using ROSETTA (Gray et al. 2003; Wang et al. 2005). The minimization step leads to pockets in which a non-clashing TS model is placed with catalytic side chains positioned with functional atoms close to the optimal geometry required for catalysis. It is then necessary to design the surrounding, non-catalytic protein residues to maximally stabilize the transition state. The conformations and identities of residues surrounding the TS model are optimized using Monte Carlo simulated annealing as described previously (Kuhlman and Baker 2000).

In other aspects, the invention involves making Diels-Alder enzymes by mutation of the scaffolds and enzymes described herein (e.g., SEQ ID NOS: 2, 4, 6, 8, and 9), or sequence or structural homologs thereof, to accommodate desired Diels-Alder substrates. Positions of such mutations and their likely involvement in substrate, transition state, or product binding, or catalytic activity, have been described.

For example, in certain embodiments, the method comprises introducing, in the amino acid sequence of SEQ ID NO:4 (DA_20_00), or a homolog thereof as described herein, from 1 to about 30, or about 1 to 20, or about 1 to 10 amino acid substitutions, insertions, and/or deletions (collectively). Such mutations are made to establish or enhance catalytic efficiency for a particular Diels-Alder substrate, such as those described herein. Generally, the Diels-Alder catalyst in accordance with these embodiments contains the catalytic residues at positions corresponding to positions 121 and 195 of SEQ ID NO:4, and otherwise has been modified in the substrate binding pocket, to bind the Diels-Alder substrates of choice.

In other embodiments, the method comprises introducing, in the amino acid sequence of SEQ ID NO:6 (DA_20_04), or a homolog thereof as described herein, from 1 to about 30, or about 1 to 20, or about 1 to 10 amino acid substitutions, insertions, and/or deletions (collectively). Such mutations are made to establish or enhance catalytic efficiency for a particular Diels-Alder substrate, such as those described herein. Generally, the Diels-Alder catalyst in accordance with these embodiments contains the catalytic residues at positions corresponding to positions 121 and 195 of SEQ ID NO:6, and otherwise has been modified in the substrate binding pocket, to bind the Diels-Alder substrates of choice.

In other embodiments, the method comprises introducing, in the amino acid sequence of SEQ ID NO:8 (DA_20_10), or a homolog thereof as described herein, from 1 to about 30, or about 1 to 20, or about 1 to 10 amino acid substitutions, insertions, and/or deletions (collectively). Such mutations are made to establish or enhance catalytic efficiency for a particular Diels-Alder substrate, such as those described herein. Generally, the Diels-Alder catalyst in accordance with these embodiments contains the catalytic residues at positions corresponding to positions 121 and 195 of SEQ ID NO:8, and otherwise has been modified in the substrate binding pocket, to bind the Diels-Alder substrates of choice.

In other embodiments, the method comprises introducing, in the amino acid sequence of SEQ ID NO:9, or a homolog thereof as described herein, from 1 to about 30, or about 1 to 20, or about 1 to 10 amino acid substitutions, insertions, and/or deletions (collectively). Such mutations are made to establish or enhance catalytic efficiency for a particular Diels-Alder substrate, such as those described herein.

The Diels-Alder catalyst may be designed to stabilize the transition state for a variety of Diels-Alder reactants. That is, amino acid substitutions, insertions and/or deletions with respect to the scaffold, or with respect to the Diels-Alder catalyzing enzymes of SEQ ID NOS: 4, 6, 8, and 9 may be selected with regard to a particular Diels-Alder reaction.

The Diels-Alder catalysts made or manufactured in accordance with these aspects are expressed and purified and/or isolated using know techniques, including in some embodiments on an industrial scale. The enzymes may be expressed in any bacterial or eukaryotic expression system, including *E. coli* or yeast expression systems, and may be purified using any suitable chromatographic step or steps, including affinity, size and/or charge-based chromatography.

EXAMPLES

Example 1

De Novo Enzyme Design

The Rosetta computational design methodology has been used to design novel enzymes (1,4) that catalyze bond breaking reactions, but bimolecular bond forming reactions present a new challenge as both substrates must be bound in the proper relative orientations. Also, previous successes with computational enzyme design have involved general acid-base catalysis and covalent catalysis, but the Diels-Alder reaction instead can be primarily influenced by modulation of molecular orbital energies (30). These examples show the design and structure of intermolecular Diels-Alder enzyme catalysts, capable of catalyzing, for example, the well-studied model Diels-Alder reaction between 4-carboxybenzyl trans-1,3-butadiene-1-carbamate and N,N-dimethylacrylamide (FIG. 2, substrates 1 and 2, respectively) (32,10).

The general protocol for Rosetta enzyme design is comprised of four steps. First, an ensemble of transition states for the reaction is built, with optimal placement of the catalytic functional groups. Each transition structure is then matched against a library of protein scaffolds using the ROSETTAMATCH algorithm. The resulting matches are then redesigned using ROSETTADESIGN so as to maximally stabilize the transition state and the placement of the catalytic residues. Designs are then ranked based on the binding energy and the satisfaction of the catalytic geometry, clustered and visually inspected. When needed, the resulting designs are then modified in silico through point mutants to improve shape complementarity (e.g., hydrophobic burial vs. more polar interfaces). The basic computational design methodology has been described in Zanghellini et al., *New algorithms and an in silico Benchmark for computational enzyme design*, Protein Science 15:2785-2794 (2006), which is hereby incorporated by reference in its entirety.

Active Site Design

The first step in de novo enzyme design is to decide on a catalytic mechanism and an associated ideal active site. Frontier Orbital Theory shows that the interaction of the highest occupied molecular orbital (HOMO) of the diene with the lowest unoccupied molecular orbital (LUMO) of the dienophile stabilizes the transition state and leads to charge transfer from diene to dienophile (30). The interaction between the HOMO and LUMO, and the stability of the transition state relative to the ground state, is increased by a hydrogen bond acceptor interacting with the carbamate NH of the diene (which increases the HOMO energy and stabilizes the positive charge accumulating in the transition state) and a hydrogen bond donor interacting with the carbonyl of the dienophile (which lowers the LUMO energy and stabilizes the negative charge accumulating in the transition state). In addition to electronic stabilization of the transition state, which quantum mechanical calculations predict can be up to 4.7 kcal/mol, binding of the two substrates in a relative orientation optimal for the reaction is expected to produce a large increase in rate through entropy reduction. Based on the above considerations, a protein with the properties shown in FIG. 2—a hydrophobic binding pocket that binds the core of the two substrates in the optimal relative orientation with appropriately placed hydrogen bond donors and acceptors—is predicted to be an effective Diels-Alder catalyst.

To design an enzyme capable of binding the transition state with the idealized hydrophobic and hydrogen bonding group placement schematized in FIG. 2, the Rosetta enzyme design methodology was employed. This approach requires three-dimensional atomic models of minimal active sites consisting of the reaction transition state and protein functional groups carrying out catalysis. We chose a carbonyl oxygen from a glutamine or asparagine to hydrogen bond with the N—H of the diene carbamate, and a hydroxyl from a serine, threonine, or tyrosine to hydrogen bond with the carbonyl oxygen of the dienophile amide moiety (FIGS. 2,4).

The transition state coordinates were obtained using quantum chemistry (QM) calculations in the presence of the specified hydrogen bond donors and acceptors. The calculations were carried out with an acetate molecule to represent the carboxylic group of an aspartate or glutamate amino acid hydrogen-bonding the N—H of the diene carbamate. To activate the dienophile 2 waters and 1 formamide, representing hydroxyl groups from tyrosine and serine residues and the amide from an asparagine/glutamine, were used to create an "oxyanion hole" to the dienophile carbonyl. While these four hydrogen-bonding groups were predicted to be most optimal for stabilizing the transition state, it was found difficult to find any scaffolds that could fit all four groups and the transition state within an active site pocket. In addition, there was concern that the acid group acting as an electron donor to the diene would be difficult to desolvate, making binding of the diene difficult. Therefore, the acid group hydrogen bonding to the N—H carbamate of the diene was replaced by an amide group, representing the functional group of a glutamine or asparagine amino acid. This change was predicted to decrease the cost of desolvation, and improve binding to the diene. In addition to replacing the acid, the oxyanion hole was replaced by a single hydroxyl group representing a serine, threonine, or tyrosine amino acid. The hydroxyl was placed in a standard hydrogen bonding geometry from the carbonyl group.

To assess the degree to which these catalytic groups can enhance the rate of the reaction, quantum mechanical transition state optimizations at the DFT B3LYP/6-31g(d) level of theory were performed. It was determined that the barrier can be lowered by as much as 4.7 kcal/mol if a glutamine residue is used for activation of the diene and a tyrosine residue as the oxyanion hole. Replacing the glutamine with a glutamate increased the barrier by 2.7 kcal/mol, arising from the loss of a hydrogen bond with the dienophile in the transition state geometry.

Figure 3:
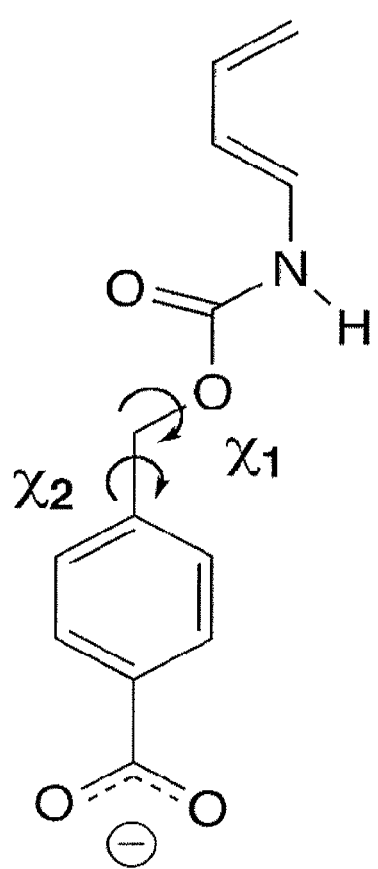
FIG. 3 shows the dihedrals in the diene molecule which were allowed to vary in order to generate the conformer ensembles during computational design.

The program SPARTAN was used to replace the methyl group on the diene with a caboxybenzyl group, since 4-Carboxybenzyl trans-1,3-butadiene-1-carbamate is the actual substrate used in the experimental assay. The diene, 4-Carboxybenzyl trans-1,3-butadiene-1-carbamate, can adopt different distinct conformers corresponding to different values of the dihedrals $\chi_1$ and $\chi_2$ (FIG. 3). Since continuous optimization of these free degrees of freedom during the active site placement search is impossible, a discrete ensemble of conformers was generated where each of the dihedral is uniformly sampled every 60 degrees. Each conformation generated was checked for an internal clash, defined as a distance of less than 3.2 Å between two atoms separated by more than two bonds. This clash filter reduced the number of transition states from a total of 36 down to a total of 15 final transition structures.

The geometry of the transition state structure in the carbon-carbon bond forming region differs significantly from the geometries of the product or the two substrates placed in the productive orientation. Although it is desired to optimally stabilize the transition state to increase catalytic rate, it is also necessary for the protein pocket to be able to accommodate (1) the two substrates bound in the relative orientation that will lead to the transition state and (2) the product of the reaction. To ensure that the designed model would accommodate all these steps along the reaction pathway, composite active site descriptions were built using the program SPARTAN. A model of the two substrates optimally oriented for catalysis, and the product of the reaction was generated. For the product, the chair conformation is favored at equilibrium in solution, but the two carbon-carbon bonds formed by the Diels-Alder reaction leads initially to a boat conformation that then relaxes to the chair conformation. Therefore, the product model included in the composite transition state is in the boat conformation. The substrate and product models were then overlaid with the quantum mechanical derived transition state model in order to generate a single composite active site model. The choice of the superimposition method was somewhat arbitrary. The three models (substrate/transition state/product) are superimposed on carbamate portion of the molecule since it is part of the core of the reaction and precise interactions were to be made with that portion of the molecule.

Figure 6:
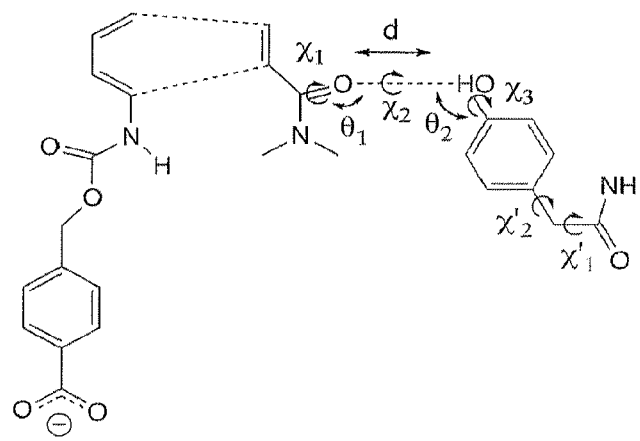
FIG. 6 shows the geometrical parameters used to place the second catalytic side-chain functional group in active site descriptions. The idealized geometries are listed, as well as the deviation (tolerance) used both for generating the discrete ensemble of rigid-body placements of transition state consensus structures, and for defining the constraint energy for minimization.

Finally, the functional groups from the catalytic residues are placed to lead to active site descriptions. Two different arrangements were considered: a glutamine H-bonding to the diene carbamate N—H, and either (1) a serine or (2) a tyrosine as an H-bond donor to the dienophile carbonyl (FIG. 4). Since both catalytic residues are stabilizing the transition state through electron-donating/electron-withdrawing effect of H-bonds to donors/acceptors on the dienophile/diene, equilibrium values for H-bond geometries were used (FIG. 5, FIG. 6).

A diverse ensemble of $1.3 \times 10^{11}$ distinct minimal active sites were generated by systematically varying the identity and rotameric state of the catalytic side chains, the hydrogen bonding geometry between these residues and the transition state, and the internal degrees of freedom of the transition state.

Scaffold Matching and Active Site Placement

A library of 207 protein scaffolds was used for active site placement (see Table 1). The scaffolds were selected such that a high-resolution crystal structure was available, and that expression in *Escherichia coli* was possible and documented. Each scaffold is equipped with one grid to mark the spatial extension of the pocket, and one grid that discretizes the pocket backbone positions for speeding up Van der Waals clash calculations (1).

The ROSETTAMATCH algorithm searches the library of protein scaffolds, stripped of all amino acid side chains, for pockets that fit the ligand in the correct orientation relative to each of the catalytic residues when coming off specified positions of the scaffold backbone. ROSETTAMATCH algorithm employs hashing to identify positions in a set of input protein scaffolds that support the construction of a specified constellation of catalytic residues. For each composite active site description, candidate catalytic sites were generated in the scaffold library. At each position in the active site pockets on each scaffold, each rotamer for each catalytic sidechain is placed and an ensemble of composite transition structures are placed so as to satisfy the geometrical parameters as described for the active site. The positions of the composite transition structure within the scaffold backbone are recorded in a six-dimensional (6D) hash. To maximize the number of solutions, large sets of sidechain rotamers were generated from each base rotamer from the Dunbrack backbone dependent rotamer library (3). Extra side-chain conformations, sampling the range defined between the mean value (the base rotamer) of each dihedral angle and +/−1/n standard deviation (where n is either 1 or 2), were generated. For each side-chain dihedral, this procedure leads to up to 7 discrete values. For instance, a total of 9702 rotamers are enumerated for asparagine/glutamine, and 81 for a tyrosine.

For each placed rotamer, an ensemble of rigid-body placements of the transition state structure is generated from the functional atoms of the sidechain, based on the parameters summarized in FIGS. 5 and 6. For each placed rotamer, thousands of different rigid-body orientations of the transition state structure are placed (around 7700 for the first catalytic residue, and around 2600 for the second). The total number of combinations evaluated by the algorithm at each position in the scaffold is more than 75,000,000 combinations for the first catalytic residue, and more than 200,000 for the second.

If considered in its entirety, the active site placement problem is one of combinatorial explosion, with a theoretical search space of more than $1.3 \times 10^{11}$ possibilities for the 15 transition state structures. However, the algorithm efficiently decreases the complexity of the search by aggressive pruning. The ensembles of rigid-body placement are first further trimmed based on their steric clash with the backbone (N,C, $C\alpha$,O) and $C\beta$ atoms. Previous uses of ROSETTAMATCH did not consider clash checks with the $C\beta$, but only the protein backbone heavy atoms. Inclusion of the $C\beta$ stems from the observation that previous active site placements by ROSETTAMATCH tended to lead to a lot of contacts between the placed transition state structure and the backbone atoms, resulting in glycines being chosen at the design stage in the binding pocket. The Van der Waals energy term is used to estimate the steric energetics between the transition state structure and these atoms, with a cut-off set to 5.0 energy units.

Following the construction of the hash table, which scales linearly with the number of scaffold positions and number of sidechain rotamers, the hash is examined for transition structure positions compatible with all catalytic constraints; such positions are termed "matches". The size of the bins for hashing are set to 0.6 Å (hashing on the center of mass rigid-body) and 10°.

Once a match is found, ROSETTAMATCH checks that the placed catalytic side-chains do not have significant steric repulsion with each other. Every match with a total steric repulsion greater than 1.0 energy unit was discarded. To evaluate whether a match was sufficiently buried, key atoms of the transition state structure (the atoms corresponding, in the transition state, to the product cyclohexene carbons) are tested for being in the grid that defines the active site pocket of each scaffold. To ensure even sampling, and avoid collecting millions of matches at the same positions, only the first 250 matches that occur in the same scaffold with the same catalytic residues at the same position in the pocket are kept.

Because of the multiple steps of pruning and clustering, the final number of matches generated by the algorithm was on the order of 500,000. Compared with the theoretical number of active sites sampled ($1.3 \times 10^{11}$), this result shows that the likelihood of finding the specific geometrical arrangement of a minimal active site in around 200 scaffolds is on the order of 3 per million.

Each match generated by the ROSETTAMATCH method is then minimized, and the rest of the pocket designed and minimized using ROSETTADESIGN using the same algorithms and parameter as described in (1, 4). A major difference with the previously published protocol deals with the definition of identities of the residues lining up the pocket that are redesigned. Residues whose $C\beta$ is within 8 Å of any atoms of the transition state structure, or whose $C\beta$ is within 10 Å of any such atoms but with a $C\alpha$-$C\beta$ vector pointing toward the transition state structure, may be redesigned to any hydrophobic or polar residue, excluding GLY and PRO (AILVYWFCMHQNST). Charged residues are only allowed in positions in the scaffold where the same charge residue is present in the wild-type structure. All the other residues, with a distance from $C\beta$ to any atom of the transition state structure less than 12 Å, are simply allowed to repack. At the end of this protocol, each design has been scored and the energy values can be used for filtering.

Selection of the designs for experimental characterization was done as follows.

1. The designs were filtered by constraint score, where constraint scores lower than 1.0 were selected.
2. The designs were filtered on total transition structure binding score, where the best 10% by score were selected. For the composite transition structures, this typically leads to a score lower than −12 energy units.
3. This list was clustered into scaffolds, meaning that all the matches that were found and designed in the same scaffold were gathered into the same directory.
4. Each of these clusters was then further clustered via spatial positioning of the transition state structure using a standard iterative partitioning clustering scheme. The clustering is based on the all-atom RMSD between the heavy atom the consensus transition state structure.
5. The best scoring designs for each of these clusters are manually inspected.
6. In some cases, point mutations are made in silico to the accepted designs, and the energy of the mutation is estimated by repacking, re-minimizing, and rescoring the structure. The criteria for point mutations are the following. Since it was anticipated that a Diels-Alder-catalyzing protein needs a relatively hydrophobic pocket, mutations that would convert an otherwise polar pocket into a more hydrophobic pocket without decreasing the score of the ligand by more than 2 units were accepted. Similarly, mutations that would improve the general shape complementarity of the transition state structure binding, as measured by the algorithm SC which is part of the crystallographic package CCP4 (5, 6), were accepted, sometimes at the expense of the total score, provided that the mutations again would not decrease the score by more than 2 units. Finally, when possible, reversion of mutated residue to WT when the mutations did not contribute significantly to the total transition state structure binding energy were made. All designs accepted for experimental characterization had fewer than 25 mutations from WT.

The highest ranked 54 design models were selected for experimental validation.

Experimental Characterization of Designs

Genes for the 54 highest-ranking designs were synthesized with a C-terminal 6-histidine affinity tag and expressed in *E. coli*. Individual proteins were purified using affinity chromatography. Only 24 of the designs were soluble. The reduced solubility is likely due to the large hydrophobic pocket needed to bind the core of the transition state, which could well lead to collapse or aggregation.

The Diels-Alder reactions were performed in PBS, at 25° C., with 4% DMSO. The DMSO came from the diene, for which the stock solution (100 mM) was made in DMSO and always diluted such that the final reaction would contain 4% DMSO. After incubation of the desired amount of diene and dienophile in the presence or absence of the protein, time points were taken of the reaction (5 μL) and quenched in a solution of 80:20 acetonitrile:water with 0.1% formic acid and 1 mM Benzoic Acid (95 μL). This reaction was incubated for 5 minutes and then the precipitated protein filtered using a Millipore multiscreen solvinert filter plate (Product Number: MSRLN0450). 20 μL of the filtered quench solution was then injected and analyzed using a liquid chromatography-tandem mass spectroscopy (LC-MSMS) assay.

One design (DA_20_00) showed an increased activity over the background reaction. This active design (DA_20_00) was created from a 6-bladed beta barrel propeller scaffold (PDB-ID 1E1A; a diisopropylfluorophosphatase from *Loligo vulgaris*). The amino acid sequence of the scaffold with respect to the original design DA_20_00 is shown in FIG. 7. The tertiary structure of the scaffold is illustrated in FIG. 8, and local secondary structures displayed in FIG. 9. As in many native beta propeller enzymes, the functional groups that play key roles in catalysis—a glutamine oxygen and a tyrosine hydroxyl provide the activating hydrogen bonds—are located in the middle of one side of the propeller. The rest of the pocket is lined with hydrophobic residues that form a tight shape-complementary surface (FIG. 10A).

A second enzyme, based on a ketosteroid isomerase scaffold, was also identified. The amino acid sequence of this enzyme is shown in FIG. 20, with active site residues identified.

Active Site Optimization: Round 1

Upon identification of an active Diels-Alder catalyst (DA_20_00), site-directed mutagenesis was performed in order to optimize the active site. Active site mutations were picked through a visual assessment of the designed active site, in which positions that had the potential to make new contacts to the diene or dienophile substrate upon mutation were identified. All mutagenesis was performed following the Kunkel protocol (8), using oligonucleotides designed using the Stratagene primer design online tool. After sequence verification of the mutated genes, protein was expressed and purified as described above.

In addition to the variants, the original active Diels-Alder enzyme (DA_20_00) and an inactive variant of the same protein (DA_20_01) were expressed and assayed, in triplicate, along side as a control.

A total of 43 variants were assayed using the standard activity assay. The observed activities are described in Table 2. In Table 2, the Expression column provides the number of times the mutant was expressed; the Observed column reports the raw signal level out of the mass-spec for the product (the Observed column is not normalized nor background corrected); the Concentration column provides the concentration of the protein after large-scale expression. The enzymes are concentrated/diluted to reach 1 and 10 mM for assays.

TABLE 2

Active Site Mutations Made in First Optimization Round

| Expression | Original | Residue | Target | Observed | Concentration | mM | mM |
|---|---|---|---|---|---|---|---|
| 1 | A | 21 | I | 229 | 73 | 1 | 10 |
| 1 | A | 21 | T | 992 | 200 | 1 | 10 |
| 1 | A | 21 | V | 366 | 200 | 1 | 10 |
| 1 | I | 72 | F | 527 | 200 | 1 | 10 |
| 1 | I | 72 | K | 504 | 200 | 1 | 10 |
| 1 | I | 72 | R | 387 | 200 | 1 | 10 |
| 1 | A | 74 | C | 1365 | 200 | 1 | 10 |
| 1 | A | 74 | L | 1760 | 200 | 1 | 10 |
| 1 | A | 74 | S | 661 | 200 | 1 | 10 |
| 1 | A | 74 | T | 1913 | 200 | 1 | 10 |
| 1 | M | 90 | F | 304 | 133 | 1 | 10 |
| 1 | M | 90 | I | 426 | 200 | 1 | 10 |
| 1 | A | 120 | I | 309 | 28 | 1 | 10 |
| 1 | A | 120 | V | 301 | 149 | 1 | 10 |
| 1 | L | 148 | F | 411 | 200 | 1 | 10 |
| 1 | L | 148 | K | 321 | 83 | 1 | 10 |
| 1 | A | 175 | C | 410 | 200 | 1 | 10 |
| 1 | A | 175 | L | 349 | 200 | 1 | 10 |
| 1 | K | 225 | F | 393 | 200 | 1 | 10 |
| 1 | S | 271 | C | 507 | 157 | 1 | 10 |
| 1 | S | 271 | T | 537 | 200 | 1 | 10 |
| 1 | S | 271 | V | 447 | 133 | 1 | 10 |
| 1 | A | 272 | S | 565 | 200 | 1 | 10 |
| 1 | H | 287 | K | 520 | 200 | 1 | 10 |
| 1 | H | 287 | Y | 330 | 200 | 1 | 10 |
| 1 | Active | 20 00 | 1 | 606 | 200 | 1 | 10 |
| 1 | Active | 20 00 | 2 | 624 | 200 | 1 | 10 |
| 1 | Active | 20 00 | 3 | 434 | 200 | 1 | 10 |
| 1 | Inactive | 20 01 | 1 | 287 | 200 | 1 | 10 |
| 1 | Inactive | 20 01 | 2 | 288 | 200 | 1 | 10 |
| 1 | Inactive | 20 01 | 3 | 314 | 200 | 1 | 10 |
| 1 | — | Background | — | 331 | — | 1 | 10 |
| 2 | A | 21 | C | 1453 | 2 | 4 | 10 |
| 2 | I | 72 | Y | 1410 | 93 | 4 | 10 |
| 2 | A | 74 | I | 8282 | 200 | 4 | 10 |
| 2 | M | 90 | L | 1483 | 175 | 4 | 10 |
| 2 | A | 120 | C | 1233 | 200 | 4 | 10 |
| 2 | A | 120 | L | 1408 | 75 | 4 | 10 |
| 2 | I | 146 | F | 1316 | 175 | 4 | 10 |
| 2 | L | 148 | F | 1646 | 200 | 4 | 10 |
| 2 | L | 148 | R | 1144 | 200 | 4 | 10 |
| 2 | I | 172 | W | 1505 | 200 | 4 | 10 |
| 2 | A | 175 | T | 1207 | 200 | 4 | 10 |
| 2 | K | 225 | Y | 1468 | 121 | 4 | 10 |
| 2 | S | 271 | A | 1984 | 200 | 4 | 10 |
| 2 | A | 272 | C | 1785 | 200 | 4 | 10 |
| 2 | A | 272 | T | 1723 | 184 | 4 | 10 |
| 2 | A | 272 | V | 1246 | 102 | 4 | 10 |
| 2 | H | 287 | F | 1308 | 200 | 4 | 10 |
| 2 | H | 287 | Y | 1262 | 26 | 4 | 10 |
| 2 | Active | 20 00 | 1 | 1569 | 157 | 4 | 10 |
| 2 | Active | 20 00 | 2 | 1574 | 200 | 4 | 10 |
| 2 | Active | 20 00 | 3 | 2027 | 200 | 4 | 10 |
| 2 | Inactive | 20 01 | 1 | 1295 | 200 | 4 | 10 |
| 2 | Inactive | 20 01 | 2 | 1133 | 169 | 4 | 10 |
| 2 | Inactive | 20 01 | 3 | 1157 | 200 | 4 | 10 |
| 2 | — | Background | — | 1293 | — | 4 | 10 |

From this set, three mutations looked particularly promising, A21T, A74I, and S271A. This set of three was recombined in a combinatorial fashion using Kunkel mutagenesis. Sequenced-verified mutants were expressed, purified, and assayed. The results are reported in FIG. 11. A74I alone produced a 16.8-fold enhancement over the original design. The triple mutant, which showed the largest increase in activity (20.5 fold rate enhancement over DA_20_00), was termed DA_20_04 and used as the new WT in a second round of active site optimization. An alignment of the original design and DA_20_04 is shown in FIG. 12.

Active Site Optimization: Round 2

A second round of active site optimization was conducted on DA_20_04. In round 2, the number of mutations screened was increased to 176 variants in order to allow for a larger breath of mutations to be made. Mutations were picked as in the first round of mutagenesis, except that we also had MD simulations to for guidance. Most noteworthy is the variation of residue 272. Additional mutations were allowed at this position since molecular dynamic simulations suggested that a larger amino acid here would bolster the catalytic tyrosine (Y121) into place.

Since it was unreasonable to prepare the 176 enzyme variants in large scale, a plate assay was developed in which colonies directly from a Kunkel mutagenesis (8) reaction could be screened. Kunkel mutagenesis reactions were transformed directly into BL21(DE3)™ (Invitrogen) in order to generate each of the desired mutants. Four colonies from each plated reaction was picked and grown at 37° C. in 0.5 mL of LB-Kanamycin overnight. These starter cultures were then used to inoculate an expression culture, in which 20 μL of the starter culture was added to 1 mL of TB-Kanamycin. This culture was grown for 2-3 hours at 37° C., after which 50 μL of 10 mM IPTG was added to each well (0.5 mM Final) in order to induce expression. The cells were then grown for 24 hours at 18° C., harvested, and stored at −20° C. until ready for assaying. To assay, crude cell lysate was prepared by resuspending the cells in 500 uL of PBS and lysing through 3 freeze/thaw cycles (15 minutes at −80° C., 40 minutes at 25° C.), followed by centrifugation at 4000 rpm for 30 minutes. 434 of the supernatant was incubated with 1 mM diene and 10 mM dienophile for two hours at room temperature. Samples from each reaction were then quenched and product detected using a liquid chromatography-tandem mass spectroscopy.

For each plate a set of four wells with DA__20__04 and four wells with DA__20__01 (an inactive variant) were grown as positive and negative controls in order to account for plate-to-plate variability. Since each variant was not sequenced and the mutagenesis procedure is not 100% efficient, the screened colonies for each variant resulted in a mix of WT and mutants. To help remove some of this noise, samples showing WT activity were discarded if at least 2 of the other colonies picked from that Kunkel reaction did show an effect on activity (either greater or less than WT). Using this method of curation ~10% of the data was discarded as failed mutagenesis reactions, which corresponds well to the efficiency of Kunkel mutagenesis. For each mutation the average of the observed product formation from the four colonies screened was compared to the background and WT product formation in the corresponding plate. The relative effect of each mutation was calculated. Mutations within 20% of background were considered to have killed activity, less than 20% of WT were considered to have decreased activity, more than 20% greater than WT were considered to increase activity, and the remaining mutations either had no effect or all four mutagenesis reactions failed. Table 2 depicts the results for each of the variants assayed in the second round.

TABLE 3

Active site mutations in second optimization round

| Current AA | Sequence Residue # | Target AA | Relative Effect on Activity |
|---|---|---|---|
| G | 19 | A | 0.03 |
| G | 19 | S | 0.67 |
| G | 19 | C | 0.51 |
| G | 19 | T | 0.38 |
| G | 19 | V | −0.06 |
| G | 19 | I | −0.02 |
| G | 19 | L | −0.26 |
| G | 19 | P | 0.03 |
| T | 21 | V | −0.22 |
| T | 21 | I | 0.43 |
| T | 21 | L | 0.06 |
| T | 21 | N | −0.11 |
| G | 22 | A | 0.19 |
| G | 22 | S | 0.37 |
| G | 22 | C | 0.02 |

TABLE 3-continued

Active site mutations in second optimization round

| Current AA | Sequence Residue # | Target AA | Relative Effect on Activity |
|---|---|---|---|
| G | 22 | T | −0.07 |
| G | 22 | V | 0.34 |
| G | 22 | I | −0.14 |
| G | 22 | L | −0.12 |
| G | 22 | P | 0.46 |
| P | 36 | A | 0.24 |
| P | 36 | S | 0.35 |
| P | 36 | C | −0.02 |
| P | 36 | T | 0.20 |
| P | 36 | V | −0.07 |
| P | 36 | I | −0.11 |
| P | 36 | L | −0.07 |
| Y | 37 | F | 0.11 |
| Y | 37 | W | 0.45 |
| Y | 37 | R | 0.07 |
| I | 72 | F | 0.11 |
| I | 72 | Y | 0.43 |
| I | 72 | W | 0.63 |
| I | 72 | M | 0.21 |
| I | 72 | K | 0.28 |
| I | 72 | R | 0.12 |
| P | 73 | A | 0.26 |
| P | 73 | S | 0.11 |
| P | 73 | C | 0.06 |
| P | 73 | T | −0.04 |
| P | 73 | V | −0.07 |
| P | 73 | I | 0.35 |
| P | 73 | L | 0.11 |
| I | 74 | F | 0.16 |
| I | 74 | Y | 0.34 |
| I | 74 | W | 0.52 |
| I | 74 | H | −0.09 |
| I | 74 | M | 0.48 |
| I | 74 | N | 0.13 |
| I | 74 | Q | 0.25 |
| G | 75 | A | 0.45 |
| G | 75 | S | 0.31 |
| G | 75 | C | 0.25 |
| G | 75 | T | 0.25 |
| G | 75 | V | 0.05 |
| G | 75 | I | 0.50 |
| G | 75 | L | 0.38 |
| G | 75 | P | −0.17 |
| M | 90 | I | −0.13 |
| M | 90 | L | 0.45 |
| M | 90 | F | −0.05 |
| A | 120 | S | 0.08 |
| A | 120 | C | −0.05 |
| A | 120 | T | −0.08 |
| A | 120 | P | 0.01 |
| A | 120 | L | −0.09 |
| A | 120 | G | 0.91 |
| Y | 121 | K | 0.00 |
| Y | 121 | R | 0.00 |
| T | 133 | A | 0.23 |
| T | 133 | S | 0.73 |
| T | 133 | C | 0.20 |
| T | 133 | V | −0.03 |
| T | 133 | I | −0.05 |
| T | 133 | L | 0.15 |
| T | 133 | P | −0.11 |
| P | 135 | A | 0.91 |
| P | 135 | S | 0.48 |
| P | 135 | C | 0.04 |
| P | 135 | T | −0.05 |
| P | 135 | V | 0.10 |
| P | 135 | I | −0.04 |
| P | 135 | L | −0.02 |
| P | 135 | G | 0.20 |
| I | 146 | F | 0.23 |
| I | 146 | Y | 0.04 |
| I | 146 | W | 0.64 |
| I | 146 | K | 1.26 |
| L | 148 | F | 0.12 |
| L | 148 | Y | −0.01 |

TABLE 3-continued

Active site mutations in second optimization round

| Current AA | Sequence Residue # | Target AA | Relative Effect on Activity |
|---|---|---|---|
| L | 148 | W | −0.04 |
| L | 148 | K | 0.01 |
| L | 148 | R | 0.01 |
| Q | 149 | K | 0.57 |
| Q | 149 | R | 1.63 |
| Q | 149 | F | 0.82 |
| Q | 149 | W | 0.18 |
| Q | 149 | Y | 0.05 |
| Q | 172 | K | 1.09 |
| Q | 172 | R | 0.29 |
| Q | 172 | F | 0.33 |
| Q | 172 | W | 0.27 |
| Q | 172 | Y | 0.34 |
| A | 173 | S | 0.49 |
| A | 173 | C | 1.13 |
| A | 173 | T | 0.64 |
| A | 173 | V | 0.17 |
| A | 173 | I | −0.04 |
| A | 173 | L | 0.29 |
| A | 173 | P | 0.02 |
| A | 175 | S | 0.30 |
| G | 176 | A | −0.01 |
| G | 176 | S | −0.05 |
| G | 176 | C | −0.01 |
| G | 176 | T | 0.09 |
| G | 176 | V | 0.28 |
| G | 176 | I | 0.00 |
| G | 176 | L | 0.03 |
| G | 176 | P | −0.08 |
| Q | 195 | H | 0.09 |
| Q | 195 | S | 0.07 |
| Q | 195 | A | 0.18 |
| P | 196 | A | 0.65 |
| P | 196 | S | 0.39 |
| P | 196 | C | 0.34 |
| P | 196 | T | 0.21 |
| P | 196 | V | 0.96 |
| P | 196 | I | 1.04 |
| P | 196 | L | 1.08 |
| K | 225 | A | 0.72 |
| K | 225 | P | 0.76 |
| K | 225 | W | 0.14 |
| G | 226 | A | 0.14 |
| G | 226 | S | −0.11 |
| G | 226 | C | −0.03 |
| G | 226 | T | 0.00 |
| G | 226 | V | 0.65 |
| G | 226 | I | 0.79 |
| G | 226 | L | 0.04 |
| G | 226 | P | −0.04 |
| A | 229 | S | 0.24 |
| A | 229 | C | −0.05 |
| A | 229 | T | −0.12 |
| A | 229 | V | −0.06 |
| A | 229 | I | −0.04 |
| A | 229 | L | −0.08 |
| A | 229 | P | 0.09 |
| G | 230 | A | 0.34 |
| G | 230 | S | 0.23 |
| G | 230 | C | 0.23 |
| G | 230 | T | 0.17 |
| G | 230 | V | 0.37 |
| G | 230 | I | −0.01 |
| G | 230 | L | 0.13 |
| G | 230 | P | 0.04 |
| A | 272 | S | 0.32 |
| A | 272 | C | 0.56 |
| A | 272 | T | 0.23 |
| A | 272 | V | 0.15 |
| A | 272 | I | 0.28 |
| A | 272 | L | 0.17 |
| A | 272 | M | 0.11 |
| A | 272 | F | 0.09 |
| A | 272 | Y | 0.18 |
| A | 272 | P | 0.07 |
| A | 272 | N | 2.44 |
| A | 272 | Q | 0.11 |
| T | 285 | A | 0.65 |
| T | 285 | V | 0.09 |
| T | 285 | I | −0.04 |
| T | 285 | L | 0.00 |
| T | 285 | P | 0.66 |
| H | 287 | L | 0.06 |
| H | 287 | M | 0.13 |
| H | 287 | N | 0.34 |
| H | 287 | Q | 0.36 |

Mutations from this set were recombined with one another if they showed an increase in activity, or they showed no effect on activity but one of the four colonies showed a significant increase in activity. The results of the combinatorial library are as shown in Table 4.

TABLE 4

Recombination of active site mutations.

Mutations Recombined

| Mutation | Mutation | Effect on |
|---|---|---|
| Neg_Control | DA_20_01 | 0 |
| Pos_Control | DA_20_04 | 1 |
| A272N | 166 | 2.44 |
| Q149R | 95 | 1.63 |
| I146K | 88 | 1.26 |
| A173C | 105 | 1.13 |
| Q172K | 99 | 1.09 |
| A120G | 67 | 0.91 |

COMBINATORIAL MUTANTS (4 colonies/Kunkel Assayed)

| | | | | |
|---|---|---|---|---|
| DA 20 08 | 166 | 95 | 105 | 67 |
| DA_20_09 | 166 | 95 | 99 | 67 |
| DA_20_10 | 166 | 95 | 105 | |
| DA_20_11 | 166 | 95 | 99 | |
| DA_20_12 | 166 | 95 | 67 | |
| DA_20_13 | 166 | 88 | 105 | 67 |
| DA_20_14 | 166 | 88 | 99 | 67 |
| DA_20_15 | 166 | 88 | 105 | |
| DA_20_16 | 166 | 88 | 99 | |
| DA_20_17 | 166 | 88 | 67 | |
| DA_20_18 | 166 | 95 | | |
| DA_20_19 | 166 | 88 | | |
| DA_20_20 | 166 | 105 | | |
| DA_20_21 | 166 | 99 | | |
| DA_20_22 | 166 | 67 | | |
| DA_20_23 | 95 | 105 | | |

Combinatorial Mutation Results

| Variant | Relative Effect on Activity |
|---|---|
| DA_20_04_105 | 2.20 |
| DA_20_04_166 | 2.82 |
| DA_20_04_67 | 0.57 |
| DA_20_04_88 | 0.65 |
| DA_20_04_95 | 1.09 |
| DA_20_04_99 | 0.80 |
| DA_20_08 | 2.93 |
| DA_20_09 | 0.50 |
| DA_20_10 | 7.96 |
| DA_20_11 | 3.41 |
| DA_20_12 | 2.00 |
| DA_20_13 | 0.71 |
| DA_20_14 | −0.21 |
| DA_20_15 | 0.05 |

TABLE 4-continued

Recombination of active site mutations.

| | |
|---|---|
| DA_20_16 | 0.00 |
| DA_20_17 | −0.13 |
| DA_20_18 | 2.85 |
| DA_20_19 | −0.19 |
| DA_20_20 | 4.35 |
| DA_20_21 | 0.99 |
| DA_20_22 | 2.10 |
| DA_20_23 | 3.25 |

DA_20_10 showed the most significant activity and was therefore used as the new WT. In order to validate the sequence and activity, the variant (and the combinatorial variants that make up DA_20_10) were sequenced, expressed, purified, and assayed using the standard protocol described for the first round of mutagenesis. The activity observed for each of the validated mutants is shown in FIG. 13. As shown, the triple mutant DA_20_10 produced 154.9 nM of product/hour under the test conditions, as compared to 21.9 for DA_20_04. An alignment of DA_20_04 and DA_20_10 is shown in FIG. 14.

To summarize the optimization rounds, residues contacting the transition state in DA_20_00 were mutated individually to sets of residues predicted to retain or improve transition state binding and bolster the two catalytic residues. Six mutations were found that in combination increase overall catalytic efficiency by roughly 2200-fold over the original design model, DA_20_00; the protein with these six additional mutations is designated DA_20_10 (FIGS. 12 and 14). Three of the mutations (FIG. 6C) likely improve the packing around the transition state (A74I, A21 T) or catalytic glutamine (A173C). Two of the mutations likely improve the overall electrostatic complementarity with the bound substrates and transition state: Q149R hydrogen bonds to the carboxylate on the diene and S271A makes the dienophile environment more non polar. The last mutation (A272N) reverts a designed alanine residue back to the native asparagine: molecular dynamics simulations suggested that the catalytic tyrosine can flip into an alternative conformation not positioned to activate the dienophile, and a larger residue at 272, such as the native asparagine, was predicted to hold the tyrosine in the conformation required for catalysis.

To determine whether the observed activity depends on the designed active site, we investigated the contributions of the designed catalytic residues in DA_20_10 to catalysis. Glutamine 195 was mutated into a glutamate (Q195E) and tyrosine 121 was mutated into a phenylalanine (Y121F). We had originally incorporated a glutamine rather than a glutamate at this position, despite the fact that the carboxylate should make a stronger hydrogen bond with the diene carbamate. This hydrogen bond should increase the energy of the diene HOMO (and thus decrease the energy gap with the dienophile LUMO), and more greatly stabilize the transition state. However, we were concerned that the substantial free energy cost of desolvating the carboxylate would considerably reduce binding affinity for the diene. The glutamine can also hydrogen bond to the dienophile, and QM calculations suggest that the concerted interaction with a catalytic tyrosine and glutamine can lower the activation energy 2 kcal/mol more than the original tyrosine and glutamate. Experimental characterization of the Q195E mutation showed almost complete loss of activity (450-fold), illustrating the sensitivity of the enzyme to the details of the designed active site. The Y121F mutation decreases catalytic activity by 27-fold, consistent with the removal of a hydrogen bond that contributes to dienophile binding, stabilizes the dienophile LUMO, and is enhanced in the transition state. The wild-type scaffold was also assayed and did not show any measurable activity.

Kinetic Characterization

The kinetics of the DA_20_10 catalyzed reaction was characterized by measuring the dependence of the reaction velocity on the concentration of both diene and dienophile. See FIG. 15. The kinetic parameters for DA_20_10 and DA_20_00, including with respect to various catalytic antibodies, are summarized in Table 5. The effective molarity (kcat/kuncat) of DA_20_10 is 100 M, and the rate enhancement (kcat/(kuncat*KM_diene)) in the presence of saturating dienophile and limiting diene is $1.0 \times 10^5$. At high substrate concentrations DA_20_10 proceeds for more than 30 turnovers before the enzyme loses activity. At higher enzyme concentrations more than 80% of the diene substrate is converted to product. These properties demonstrate that de novo designed enzymes could be useful as catalysts in production level chemical synthesis.

TABLE 5

Kinetic Parameters for DA_20_00 and DA_20_10

| Catalyst | $k_{cat}$ (hr$^{-1}$) | $K_{M\text{-}diene}$ (mM) | $K_{M\text{-}dienophile}$ (mM) | a |
|---|---|---|---|---|
| DA_20_00 (298K) | 0.01 ± 0.002 | 3.53 ± 1.5 | 146 ± 2.5 | — |
| DA_20_10 (298K) | 2.44 ± 0.3 | 0.98 ± 0.2 | 58.1 ± 14 | 1.7 ± 0.7 |
| mAb 7D4 (310K) | 0.21 | 0.96 | 1.70 | 1 |
| mAB 4D5 (310K) | 0.21 | 1.60 | 5.90 | 1 |

The errors represent the calculated 95% confidence interval. The parameter a describes the cooperativity of binding between the two substrates: a value greater than one indicates negative cooperativity, whereas a value lower then one indicates positive cooperativity. α could not be determined for DA_20_00. Kinetic parameters for catalytic antibodies 7D4 and 4D5 were taken from (10, 17). The $k_{uncat}$ for the Diels-Alder reaction at 298K was found to be $2.44 \times 10^2$ M$^{-1}$ hr$^{-1}$, in good agreement with the previously reported value at 310K of $4.29 \times 10^{-2}$ M$^{-1}$ hr$^{-1}$.

The kinetic parameters of DA_20_10 compare favorably with the best catalytic antibodies elicited for this Diels-Alder reaction (Table 4). The kcat of DA_20_10 is 10-fold greater than those of 7D4 (10) and 4D5 (17), but this may be an underestimate because the catalytic antibodies were measured at 310K rather than 298K. The KM for the diene is in the same millimolar range as the catalytic antibodies, but the KM for the dienophile is one order of magnitude worse, which is not surprising given the power of the immune system to produce high affinity binding proteins to arbitrary ligands. Because of the weaker KM for the dienophile, the rate enhancement with saturating diene and limiting dienophile (kcat/(kuncat*KM_dienophile), $1.7 \times 10^3$) is similar to those of the antibodies, but the effective molarity (kcat/kuncat) and the rate enhancement with saturating dienophile and limiting diene (kcat/(kuncat*KM_diene)) are both 20-fold greater than for either antibody.

Turnover and Production

To quantify the number of turnovers reached before the DA_20_10 was inactivated, a reaction was setup with 25 μM enzyme, 3 mM diene, 100 mM dienophile in a PBS solution and incubated for 160 hours. Time points were taken, quenched, and filtered, and then analyzed using the liquid chromatography mass-spectroscopy assay. A standard curve ranging from 4 mM to 0.03 mM was used to quantify the amount of product produced. The curve obtained is shown in FIG. 16.

To show that DA_20_10 was capable of production runs for chemical synthesis, and to show the effects of knocking out the catalytic residues, a set of reactions was carried out with 1 mM diene and 50 mM dienophile in PBS at 298K in the absence or presence of 200 µM protein. Timepoints were taken and measured as previously described over a period of 60 hours. The resulting plot is shown in FIG. 17.

Stereospecificity

A liquid chromatography-tandem mass spectroscopy with a chiral column was used to detect each of the four experimentally observed stereoismers. The chiral column used in this work was the same as in (10), so it was predicted that the product peaks would come out in the same order. To validate that the endo and exo products came out as expected each was synthesized, and run either separately or together to identify the endo and exo peaks. The peaks observed come out in the same order and same time as reported in Cannizzaro et al. (10).

In order to quantify the stereospecificity of DA_20_10, a reaction with 2 mM diene, 70 mM dieneophile, PBS, pH 7.4, in the presence or absence of 80 µM protein was run for 24 hr at 298K. Both reactions, with and without enzyme, were quenched at the same time by adding 475 µL of running buffer to the 25 µL reaction. The reactions were shaken for 5 minutes, centrifuged for 5 minutes, after which the organic layer was removed and analyzed with a LC-MSMS assay. 25 µL of the sample was injected onto a Diacel AD-H column, which was run using a 30 minute isocratic program of 70:30 hexanes:isopropanol with 0.1% formic acid. The same mass spectroscopy parameters used for the standard Diels-Alder product detection assay were used for this assay. The chromatograms obtained from these reactions and a standard 50 µM mix of 1:1 endo:exo product are shown diagrammatically in FIG. 18.

While the low signal observed for the exo products make the peak areas difficult to quantify, we can estimate that the relative product observed for the background reaction as approximately 3:3:47:47 at 298K. This is in good agreement with a ratio of 7:7:43:43 previously observed at 310K (10). From this we can conclude that we should be able to clearly see a peak at 3% of a reaction. For, the enzymatic reaction, the peaks areas for all but endo-3R4S are virtually identical to the background reaction peaks. Therefore the stereospecifity of DA_20_10 is likely to be greater than 97% ee.

Substrate Specificity

To experimentally determine substrate specificities each dienophile from FIG. 19 was either purchased or synthesized. The dienophiles were assayed in the presence or absence of 60 µM DA_20_10 or the H287N mutant over 30 hours with 10 mM dienophile and 0.2 mM diene at 298K in a PBS solution. A sample of the reaction was taken at four different time points, quenched, and filtered as previously described. To detect product a liquid chromatography-mass spectroscopy assay was used. The mass spectrometer was used in a selective-ion-monitoring mode and set to specifically detect the expected product from each reaction. The average area of each detected peak formed per hour was used to determine the relative amount of product formed with and without enzyme. The relative peak areas formed per hour are shown in FIG. 19.

Confirmation of Enzyme Structure

To determine the structural accuracy of the design, we solved the crystal structure of DA_20_00 with the A74I mutation. The crystal structure shows atomic level agreement with the design model, with an all-atom RMSD of 0.5 Å. The major deviation between the crystal structure and the design model is in a surface loop, which appears to be pulled back from the predicted active site (RMSD on residues 32 to 46, 0.93 Å). Consistent with the reductions in activity observed upon mutation of the designed catalytic residues, the conformations of these sidechains in the crystal structure are close to those in the design model; taken together these results strongly suggest that the experimentally observed activity is generated by the designed active site.

Discussion

The Diels-Alder reaction studied here can, in principle, produce eight different isomeric products, four of which are experimentally observed in the reaction in solution FIG. 19 (10). The computational design was directed at the transition state that yields the endo-Re product (3R,4S), which comprises 47% percent of the total product formed in the uncatalyzed reaction. Consistent with the design, DA_20_10 only catalyzes the formation of the expected 3R,4S product (>97%). The high diastereo- and enantioselectivity of DA_20_10 demonstrates the ability of the computational enzyme design protocol disclosed herein to control reaction stereoselectivity.

Besides stereoselectivity, the level of control over a chemical reaction by a designed enzyme is reflected by its substrate specificity. To investigate the substrate specificity of DA_20_10, we characterized product formation with six different dienophiles that share the same acrylamide core but have different nitrogen substituents (FIG. 19). The activity against each of the substrates was measured using a liquid-chromatography mass spectroscopy assay. The specificity of DA_20_10 was observed to highly favor the substrate for which it was designed. Even slight changes, such as adding a methyl group to the N,N-dimethylacrylamide, significantly decreased the activity of DA_20_10, consistent with the tight packing of the active site around the two substrates.

In addition to the ability to catalyze new reactions with high substrate specificity and stereoselectivity, one of the promises of de novo enzyme design is that once an initial active enzyme is engineered it can be easily modified to catalyze similar reactions with alternate substrates. To explore this possibility, we mutated histidine 287 on one side of the dienophile binding pocket to asparagine and several other residues. The H287N mutation has a substrate specificity profile different from DA_20_10, in particular there is a 13-fold switch in specificity for dienophile 2E relative to 2A, while selectivity against 2F is maintained (FIG. 19). The specificity switch may have two origins: the histidine in the crystal structure clashes with the larger substrates, and the amino group on the asparagine can hydrogen bond with the hydroxyl in 2F.

This Diels-Alderase is the first computationally designed enzyme that catalyzes a synthetically important abiological reaction, the formation of two carbon-carbon bonds from two distinct molecules, and exhibits both strong stereoselectivity and substrate specificity. The agreement between the designed and experimentally observed substrate specificity and stereoselectivity of the enzyme is notable given the importance of selectivity in organic reactions. Furthermore, the capability to rationally control both substrate specificity and stereoselectivity via designed enzymes opens up new avenues of research in both basic and applied chemistry. Although biocatalysis for drug manufacturing is extremely attractive to the chemical and pharmaceutical industries, its use has been limited by the ability to discover or evolve enzymes with the desired substrate specificity and stereoselectivity. Our results suggest that computational enzyme design provides a solution to this problem.

Example 2

Preparation of Enzyme for Selected Diels-Alder Substrates

Redesign of either DA_20_00, DA_20_04 or DA_20_10 for new substrates involves the following steps.

First, construction of a new active site model that incorporates a new transition state, substrate(s) and product(s) models for the substrate of interest. This active site may contain new active site residues (i.e. amino-acid to originate from the protein) or not, depending on the substituent on the diene and dienophile of interest.

Second, this active site can be placed in the scaffold of DA_20_00, DA_20_04 or DA_20_10 by placing the active site into the protein pocket using a hashing-based active site placement method as disclosed herein, followed by design and minimization of the rest of the pocket. Alternatively, the active site may be placed in the scaffold by superimposing the "catalytic" core of the active site model for the new substrate(s)/transition state/product(s) to the catalytic core of the active site previously placed in DA_20_00, DA_20_04 and DA_20_10. The catalytic core may be comprised of the two double bonds of the diene, the double bond of the dienophile, the two carbon-carbon bond being formed as the reaction proceeds. Other superimposition techniques are possible, for instance superimposition on substituents common to the new substrate(s)/transition state/product(s) and the one that were used for the original design of DA_20_00, DA_20_04 and DA_20_10.

Alternatively still, the active site may be placed by altering the backbone of the scaffolds of DA_20_00, DA_20_04, and DA_20_10 to accommodate the new substrate(s)/transition state/product(s). Alteration of the backbone may require the generation of a variable number of backbone models, typically on the order of 1,000 to 1,000,000.

After placement of the active site, the position of the placed substrate(s)/transition state/product(s) and/or the catalytic groups is minimized. The minimization step may include minimizing the substrate(s)/transition state/product(s) internal degrees of freedom, minimizing the protein side-chain and backbone degrees of freedom using standard force-fields, as well as rigid-body placement of the substrate(s)/transition state/product(s). The minimization step is followed by design of the rest of the protein pocket. The design step may include any number of variable positions, and an additional minimization step in the context of new sequences optimized by the design step. This subsequent minimization step may include the same features as above.

Promising designs are then ranked and selected for testing.

Exemplary reactions to be catalyzed by a Diels-Alder enzyme catalyst are illustrated in FIG. 21. Reaction (1) produces an intermediate used for the production of TAMIFLU. Reaction (2) leads to the production of a building block useful for the manufacture of the polymer PET. Reaction (3) can be used for the manufacture of vitamin B6. Reaction (4) is a reaction commonly referred to as "click chemistry."

The enzymes produced in Example 1 may be optimized to catalyze such Diels-Alder reactions, using the information and methods disclosed herein. For example, the active site of the enzyme designs disclosed herein may be altered to be less hydrophobic to accommodate more polar structures and/or to provide additional contacts for the Diels-Alder substrates and/or transition states, and may include additional hydrogen bonding and electrostatic contacts. Conversely, the active site of the designs can be altered to present a more hydrophobic interface to one or both of the substrates, such as ethylene.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

References

1. D. Rothlisberger et al., *Nature* 453, 190 (May 8, 2008).
2. A. Zanghellini et al., *Protein Sci* 15, 2785 (Dec. 1, 2006, 2006).
3. R. L. Dunbrack, Jr., F. E. Cohen, *Protein Sci* 6, 1661 (August, 1997).
4. L. Jiang et al., *Science* 319, 1387 (Mar. 7, 2008).
5. N. COLLABORATIVE COMPUTATIONAL PROJECT, *Acta Cryst* D50, 760 (1994).
6. M. C. Lawrence, P. M. Colman, *Journal of Molecular Biology* 234, 946 (1993).
7. E. Gasteiger et al., in *John M Walker (ed): The Proteomics Protocols Handbook.* (Humana Press, 2005).
8. T. A. Kunkel, P *Natl Acad Sci USA* 82, 488 (January 1985, 1985).
9. I. H. Segel, *Enzyme kinetics: behavior and analysis of rapid equilibrium and steady state enzyme systems.* (Wiley, New York, 1975), pp. xxii, 957 p.
10. C. E. Cannizzaro, J. A. Ashley, K. D. Janda, K. N. Houk, *Journal of the American Chemical Society* 125, 2489 (2003).
11. M. Benvenuti, S. Mangani, *Nat. Protocols* 2, 1633 (2007).
12. Z. Otwinowski, W. Minor, in *Methods in Enzymology: Macromolecular Crystallography, part A*. (C. W. Carter, Jr. & R. M. Sweet, Eds., 1997), vol. 276, pp. 307-326.
13. A. J. McCoy, R. W. Grosse-Kunstleve, L. C. Storoni, R. J. Read, *Acta Crystallographica Section D* 61, 458 (2005).
14. P. Emsley, K. Cowtan, *Acta Crystallographica Section D* 60, 2126 (2004).
15. G. N. Murshudov, A. A. Vagin, E. J. Dodson, *Acta Crystallographica Section D* 53, 240 (1997).
16. M. D. Winn, M. N. Isupov, G. N. Murshudov, *Acta Crystallographica Section D* 57, 122 (2001).
17. R. A. Laskowski, M. W. MacArthur, D. S. Moss, J. M. Thornton, *Journal of Applied Crystallography* 26, 283 (1993).
18. X. Jian, J. Xiaoze, L. Shiyong, *Journal of Polymer Science Part A: Polymer Chemistry* 46, 60 (2008).
19. N. Kuhnert, A. Le-Gresley, *Organic & Biomolecular Chemistry* 3, 2175 (2005).
20. D. A. Case et al. (University of California, San Francisco, 2008).
21. C. I. Bayly, P. Cieplak, W. Cornell, P. A. Kollman, *The Journal of Physical Chemistry* 97, 10269 (2002).
22. H. B. Brent, M. M. Kenneth, Jr., A. K. Peter, *Journal of Computational Chemistry* 11, 431 (1990).
23. U. C. Singh, A. K. Peter, *Journal of Computational Chemistry* 5, 129 (1984).
24. M. J. Frisch et al. (Gaussian, Inc., Wallingford Conn., 2004).
25. M. W. Mahoney, W. L. Jorgensen, *The Journal of Chemical Physics* 112, 8910 (2000).
26. H. Viktor et al., *Proteins: Structure, Function, and Bioinformatics* 65, 712 (2006).
27. S. P. Kim, A. G. Leach, K. N. Houk, *The Journal of Organic Chemistry* 67, 4250 (2002).

28. D. C. Rideout, R. Breslow, *J. Am. Chem. Soc.* 102, 7816 (1980).
29. R. Breslow, C. J. Rizzo, *Journal of the American Chemical Society* 113, 4340 (2002).
30. D. L. Boger, in *Modern Organic Synthesis: Lecture Notes.* (TSRI Press, 1999), pp. 213-272.
31. J. T. Yli-Kauhaluoma et al., *Journal of the American Chemical Society* 117, 7041 (1995).
32. V. E. Gouverneur et al., *Science* 262, 204 (Oct. 8, 1993, 1993).
33. M. S. Emily, M. W. Robert, *Angewandte Chemie International Edition* 42, 3078 (2003).
34. H. Oikawa, T. Kobayashi, K. Katayama, Y. Suzuki, A. Ichihara, *The Journal of Organic Chemistry* 63, 8748 (1998).
35. K. Katayama, T. Kobayashi, H. Oikawa, M. Honma, A. Ichihara, *Biochimica et Biophysica Acta (BBA)—Protein Structure and Molecular Enzymology* 1384, 387 (1998).
36. K. Auclair et al., *Journal of the American Chemical Society* 122, 11519 (2000).
37. T. Ose et al., *Nature* 422, 185 (2003).
38. K. Watanabe, T. Mie, A. Ichihara, H. Oikawa, M. Honma, *J Biol Chem* 275, 38393 (2000).
39. C. R. W. Guimaraes, M. Udier-Blagovic, W. L. Jorgensen, *Journal of the American Chemical Society* 127, 3577 (2005).
40. J. M. Serafimov, D. Gillingham, S. Kuster, D. Hilvert, *Journal of the American Chemical Society* 130, 7798 (2008).
41. T. M. Tarasow, S. L. Tarasow, B. E. Eaton, *Nature* 389, 54 (1997).
42. K. N. Morris et al., *P Natl Acad Sci USA* 91, 13028 (1994).
43. B. Seelig, A. Jäschke, *Chemistry & Biology* 6, 167 (1999).
44. D. Hilvert, K. W. Hill, K. D. Nared, M.-T. M. Auditor, *J. Am. Chem. Soc.* 111, 9261 (1989).
45. J. Xu et al., *Science* 286, 2345 (1999).
46. A. C. Braisted, P. G. Schultz, *Journal of the American Chemical Society* 112, 7430 (2002).

The invention claimed is:

1. A method for making an enzyme that catalyzes a Diels-Alder reaction, the method comprising:
creating a Diels-Alder active site model comprising a diene component, a dienophile component, and hydrogen bond donor and hydrogen bond acceptor amino acid functional groups positioned to support catalysis;
placing the Diels-Alder active site model in a Diels-Alder scaffold selected from *Loligo vulgaris* diisopropylfluorophosphatase, *Pseudomonas putida* ketosteroid isomerase, or a sequence homolog or structural homolog thereof having a 6-bladed beta propeller fold or an alpha+beta roll fold;
introducing mutations in the scaffold to prepare an active site having the protein functional groups in position to stabilize the Diels-Alder transition state, and having a surface complementary to the Diels-Alder transition state;
introducing mutations in the scaffold as guided by computational design and Diels-Alder assay; and
expressing the Diels-Alder enzyme and testing for the Diels-Alder enzyme activity.

2. A method for making an enzyme that catalyzes a Diels-Alder reaction, the method comprising:
providing a Diels-Alder scaffold having at least 30% sequence identity to SEQ ID NO: 2 or SEQ ID NO:9, and having a 6-bladed beta propeller fold or an alpha+beta roll fold,
introducing one or more mutations in the Diels-Alder scaffold, and
contacting the Diels-Alder scaffold with desired Diels-Alder substrate, and quantifying Diels-Alder enzyme activity to thereby create a Diels-Alder enzyme, expressing the Diels-Alder enzyme.

3. The method of claim 2, wherein the Diels-Alder scaffold has one or more mutations at positions corresponding to one or more of positions 21, 36, 37, 39, 72, 74, 90, 120, 135, 136, 144, 146, 148, 149, 173, 175, 176, 196, 225, 229, 230, 244, 269, 271, 272, and 287 of SEQ ID NO:2.

4. The method of claim 2, wherein the Diels-Alder scaffold has one or more mutations at positions corresponding to one or more of positions 86, 93, 95, 121, 118, 116, 40, 43, 39, 84, 62, 59, 58, 37, 46, 55, 97, 114, 112, 99, 82, 19, 60, 64, 16, 31, 15, 80, 27, and 56 of SEQ ID NO:9.

5. The method of claim 2, wherein from 1 to 30 mutations are introduced into the scaffold to create the Diels-Alder enzyme.

6. The method of claim 2, wherein from 1 to 20 mutations are introduced into the scaffold to create the Diels-Alder enzyme.

7. The method of claim 1, wherein the Diels-Alder active site model comprises a Diels-Alder transition state stabilized by an amino acid functional group acting as a hydrogen bond acceptor, and/or by an amino acid functional group acting as a hydrogen bond donor.

8. The method of claim 7, wherein the protein functional groups bind the substrates in the proper orientation to enhance the reaction rate.

9. The method of claim 1, wherein the diene is linear or cyclic.

10. The method of claim 1, wherein the diene has one or more heteroatoms.

11. The method of claim 1, wherein the diene has one or more substituents.

12. The method of claim 1, wherein the dienophile is substituted.

13. The method of claim 1, wherein the dienophile is unsubstituted ethene or ethyne.

14. The method of claim 1, wherein the dienophile is substituted with at least one electron-withdrawing group making the dienophile more electrophilic.

15. The method of claim 1, wherein amino acid residues around the Diels-Alder active site-model, other than the catalytic residues, are mutated to alanine or glycine residues prior to experimentally confirming Diels-Alder enzyme activity.

16. The method of claim 15, wherein active site residues are defined as amino acid residues whose $C\beta$ is within 8 Å of any atoms of the transition state structure, or whose $C\beta$ is within 10 Å of any such atoms but with a $C\alpha$-$C\beta$ vector pointing toward the transition state structure.

17. The method of claim 15, wherein the active site residues other than the catalytic residues are changed to any hydrophobic or polar residue, excluding Gly and Pro.

18. The method of claim 15, wherein at least 3 active site residues are changed to alanine.

19. The method of claim 1, wherein the scaffold is a homolog having at least 30% sequence identity to SEQ ID NO:2 or SEQ ID NO:9.

20. The method of claim 1, wherein the scaffold is a homolog having at least 50% sequence identity to SEQ ID NO:2 or SEQ ID NO:9.

21. The method of claim 1, wherein the Diels-Alder scaffold has from 5 to 30 amino acid substitutions with respect to SEQ ID NO:2, and/or from 1 to 30 amino acid insertions or deletions with respect to SEQ ID NO:2.

22. The method of claim 1, wherein the Diels-Alder scaffold has from 1 to 20 amino acid substitutions, insertions, or deletions with respect to SEQ ID NO:9.

23. The method of claim 1, wherein the Diels-Alder active site model includes a diene having a substituent of less than 30 atoms and a dienophile having a substituent of less than 30 atoms.

24. The method of claim 1, wherein the Diels-Alder scaffold has at least 30% sequence identity with SEQ ID NO:2, including amino acid substitutions at positions corresponding to one or more of positions 21, 36, 37, 39, 72, 74, 90, 120, 135, 136, 144, 146, 148, 149, 173, 175, 176, 196, 225, 229, 230, 244, 269, 271, 272, and 287 of SEQ ID NO:2.

25. The method of claim 1, wherein the Diels-Alder scaffold has at least 30% sequence identity with SEQ ID NO:9, including amino acid substitutions at positions corresponding to one or more of positions 86, 93, 95, 121, 118, 116, 40, 43, 39, 84, 62, 59, 58, 37, 46, 55, 97, 114, 112, 99, 82, 19, 60, 64, 16, 31, 15, 80, 27, and 56 of SEQ ID NO:9.

26. The method of claim 1, wherein the catalytic residue acting as a hydrogen bond acceptor is a glutamine or asparagine, and the catalytic residue acting as a hydrogen bond donor is serine, tyrosine, or threonine.

* * * * *

UNITED STATES PATENT AND TRADEMARK OFFICE
CERTIFICATE OF CORRECTION

PATENT NO.       : 8,688,427 B2
APPLICATION NO.  : 13/130260
DATED            : April 1, 2014
INVENTOR(S)      : Baker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 54 days.

Signed and Sealed this

Twenty-ninth Day of September, 2015

Michelle K. Lee
*Director of the United States Patent and Trademark Office*